(12) United States Patent  
Burns et al.

(10) Patent No.: US 11,824,291 B2  
(45) Date of Patent: *Nov. 21, 2023

(54) DEVICE WITH DISPOSABLE ELEMENT

(71) Applicant: BRUIN BIOMETRICS, LLC, Los Angeles, CA (US)

(72) Inventors: Martin F. Burns, Los Angeles, CA (US); Bill Campbell, Escondido, CA (US); David M. Giuntoli, Carlsbad, CA (US); Mark Raptis, Valley Center, CA (US); Graham O. Ross, Oceanside, CA (US)

(73) Assignee: Bruin Biometrics, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/167,610

(22) Filed: Feb. 10, 2023

(65) Prior Publication Data

US 2023/0335929 A1    Oct. 19, 2023

Related U.S. Application Data

(63) Continuation of application No. 17/751,082, filed on May 23, 2022, now Pat. No. 11,600,939, which is a (Continued)

(51) Int. Cl.
*H01R 13/405* (2006.01)
*H01R 12/70* (2011.01)
(Continued)

(52) U.S. Cl.
CPC ..... *H01R 12/7076* (2013.01); *H01R 12/7082* (2013.01); *H01R 13/405* (2013.01); (Continued)

(58) Field of Classification Search
None
See application file for complete search history.

(56) References Cited

U.S. PATENT DOCUMENTS 3,851,641 A    12/1974  Toole et al.
4,295,009 A    10/1981  Weidler
(Continued)

FOREIGN PATENT DOCUMENTS

AU    2020103438 A4    1/2021
CA    2811609           11/2011
(Continued)

OTHER PUBLICATIONS

Extended European Search Report dated Feb. 1, 2023, in European Patent Application No. 22211200.
(Continued)

*Primary Examiner* — Tho D Ta
(74) *Attorney, Agent, or Firm* — Arnold & Porter Kaye Scholer LLP

(57) ABSTRACT

The construction of a medical device having a disposable element is disclosed. Detachable elements comprising a body having a retention feature, an electrical contactor, and sensors are also disclosed. Further disclosed are detachable elements comprising a body having a hole and a retention pocket, an electrical contactor, and a printed circuit board assembly (PCB) in contact with the innermost surface of the body that forms the retention pocket. Further disclosed are detachable elements comprising a body having an opening and a printed film comprising conductive elements, where the conductive elements comprise a sensor configured to be aligned with the opening to expose the sensor. Further disclosed are reusable components having matching retention features.

18 Claims, 8 Drawing Sheets

Related U.S. Application Data continuation of application No. 17/164,706, filed on Feb. 1, 2021, now Pat. No. 11,342,696, which is a continuation of application No. 16/598,758, filed on Oct. 10, 2019, now Pat. No. 10,950,960.

(60) Provisional application No. 62/804,095, filed on Feb. 11, 2019, provisional application No. 62/744,513, filed on Oct. 11, 2018.

(51) Int. Cl.
*H01R 13/24* (2006.01)
*H01R 12/71* (2011.01)

(52) U.S. Cl.
CPC ........ *H01R 12/716* (2013.01); *H01R 13/2442* (2013.01); *H01R 13/2457* (2013.01); *Y10S 439/909* (2013.01); *Y10S 439/913* (2013.01)

(56) References Cited

U.S. PATENT DOCUMENTS

| | | | |
|---|---|---|---|
| 4,557,271 A | 12/1985 | Stoller et al. | |
| 4,857,716 A | 8/1989 | Gombrich et al. | |
| 4,860,753 A | 8/1989 | Amerena | |
| 5,001,436 A | 3/1991 | Scot | |
| 5,073,126 A | 12/1991 | Kikuchi et al. | |
| 5,284,150 A | 2/1994 | Butterfield et al. | |
| 5,292,341 A | 3/1994 | Snell | |
| 5,367,789 A | 11/1994 | Lamont | |
| 5,815,416 A | 9/1998 | Liebmann et al. | |
| 5,904,581 A | 5/1999 | Pope et al. | |
| 6,204,749 B1 * | 3/2001 | Ishihara | H01C 10/14 338/160 |
| 6,223,088 B1 | 4/2001 | Scharnberg et al. | |
| 6,254,435 B1 | 7/2001 | Cheong et al. | |
| 6,312,263 B1 | 11/2001 | Higuchi et al. | |
| 6,330,479 B1 | 12/2001 | Stauffer | |
| 6,368,284 B1 | 4/2002 | Bardy | |
| 6,370,426 B1 | 4/2002 | Campbell et al. | |
| 6,434,422 B1 | 8/2002 | Tomoda et al. | |
| 6,577,700 B1 | 6/2003 | Fan et al. | |
| 6,634,045 B1 | 10/2003 | DuDonis et al. | |
| 6,738,798 B1 | 5/2004 | Ploetz et al. | |
| 6,756,793 B2 | 6/2004 | Hirono et al. | |
| 6,963,772 B2 | 11/2005 | Bloom et al. | |
| 7,079,899 B2 | 7/2006 | Petrofsky | |
| 7,291,023 B1 * | 11/2007 | Still | G01D 11/245 439/67 |
| 7,315,767 B2 | 1/2008 | Caduff et al. | |
| 7,402,135 B2 | 7/2008 | Leveque et al. | |
| 7,783,344 B2 | 8/2010 | Lackey et al. | |
| 8,011,041 B2 | 9/2011 | Hann | |
| 8,060,315 B2 | 11/2011 | Brosette et al. | |
| 8,355,925 B2 | 1/2013 | Rothman et al. | |
| 8,390,583 B2 | 3/2013 | Forutanpour et al. | |
| 8,494,617 B2 | 7/2013 | Baker, Jr. et al. | |
| 8,648,707 B2 | 2/2014 | Franz et al. | |
| 8,690,785 B2 | 4/2014 | Lading | |
| 8,925,392 B2 | 1/2015 | Esposito et al. | |
| 9,028,407 B1 | 5/2015 | Bennett-Guerrero | |
| 9,095,305 B2 | 8/2015 | Engler et al. | |
| 9,220,455 B2 | 12/2015 | Sarrafzadeh et al. | |
| 9,271,676 B2 | 3/2016 | Alanen et al. | |
| 9,398,879 B2 | 7/2016 | Sarrafzadeh et al. | |
| 9,675,289 B2 | 6/2017 | Heaton | |
| 9,763,596 B2 | 9/2017 | Tonar et al. | |
| 9,949,683 B2 | 4/2018 | Afentakis | |
| 9,980,673 B2 | 5/2018 | Sarrafzadeh et al. | |
| 10,085,643 B2 | 10/2018 | Bandic et al. | |
| 10,166,387 B2 | 1/2019 | Bergelin et al. | |
| 10,178,961 B2 | 1/2019 | Tonar et al. | |
| 10,182,740 B2 | 1/2019 | Tonar et al. | |
| 10,188,340 B2 | 1/2019 | Sarrafzadeh et al. | |
| 10,194,856 B2 | 2/2019 | Afentakis et al. | |
| 10,206,604 B2 | 2/2019 | Bergelin et al. | |
| 10,226,187 B2 | 3/2019 | Al-Ali et al. | |
| 10,278,636 B2 | 5/2019 | Wu et al. | |
| 10,285,898 B2 | 5/2019 | Douglas et al. | |
| 10,307,060 B2 | 6/2019 | Tran | |
| 10,342,482 B1 | 7/2019 | Lisy et al. | |
| 10,383,527 B2 | 8/2019 | Al-Ali | |
| 10,420,602 B2 | 9/2019 | Horton et al. | |
| 10,441,185 B2 | 10/2019 | Rogers et al. | |
| 10,448,844 B2 | 10/2019 | Al-Ali et al. | |
| 10,463,293 B2 | 11/2019 | Maharbiz et al. | |
| 10,485,447 B2 | 11/2019 | Tonar et al. | |
| 10,898,129 B2 | 1/2021 | Burns et al. | |
| 10,950,960 B2 * | 3/2021 | Burns | H01R 13/24 |
| 10,959,664 B2 | 3/2021 | Burns et al. | |
| 11,191,477 B2 | 12/2021 | Burns | |
| 11,253,192 B2 | 2/2022 | Sarrafzadeh et al. | |
| 11,284,810 B2 | 3/2022 | Tonar et al. | |
| 11,304,652 B2 | 4/2022 | Burns et al. | |
| 11,337,651 B2 | 5/2022 | Burns et al. | |
| 11,342,696 B2 * | 5/2022 | Burns | A61B 5/14539 |
| 11,426,118 B2 | 8/2022 | Burns | |
| 11,471,094 B2 | 10/2022 | Burns et al. | |
| 11,534,077 B2 | 12/2022 | Tonar et al. | |
| 11,600,939 B2 * | 3/2023 | Burns | H01R 13/405 |
| 11,627,910 B2 | 4/2023 | Burns et al. | |
| 11,642,075 B2 | 5/2023 | Burns et al. | |
| 2001/0051783 A1 | 12/2001 | Edwards et al. | |
| 2002/0016535 A1 | 2/2002 | Martin et al. | |
| 2002/0070866 A1 | 6/2002 | Newham | |
| 2002/0112898 A1 | 8/2002 | Honda et al. | |
| 2002/0143262 A1 | 10/2002 | Bardy | |
| 2003/0009244 A1 | 1/2003 | Engleson et al. | |
| 2003/0036674 A1 | 2/2003 | Bouton | |
| 2003/0036713 A1 | 2/2003 | Bouton et al. | |
| 2003/0110662 A1 | 6/2003 | Gilman et al. | |
| 2003/0116447 A1 | 6/2003 | Surridge et al. | |
| 2003/0130427 A1 | 7/2003 | Cleary et al. | |
| 2003/0139255 A1 | 7/2003 | Lina | |
| 2004/0041029 A1 | 3/2004 | Postman et al. | |
| 2004/0046668 A1 | 3/2004 | Smith et al. | |
| 2004/0054298 A1 | 3/2004 | Masuo et al. | |
| 2004/0080325 A1 | 4/2004 | Ogura | |
| 2004/0133092 A1 | 7/2004 | Kain | |
| 2004/0147977 A1 | 7/2004 | Petrofsky | |
| 2004/0171962 A1 | 9/2004 | Leveque et al. | |
| 2004/0176754 A1 | 9/2004 | Island et al. | |
| 2004/0236200 A1 | 11/2004 | Say et al. | |
| 2004/0254457 A1 | 12/2004 | Van Der Weide | |
| 2005/0027175 A1 | 2/2005 | Yang | |
| 2005/0070778 A1 | 3/2005 | Lackey et al. | |
| 2005/0086072 A1 | 4/2005 | Fox, Jr. et al. | |
| 2005/0096513 A1 | 5/2005 | Ozguz et al. | |
| 2005/0177061 A1 | 8/2005 | Alanen et al. | |
| 2005/0203435 A1 | 9/2005 | Nakada | |
| 2005/0215918 A1 | 9/2005 | Frantz et al. | |
| 2005/0245795 A1 | 11/2005 | Goode et al. | |
| 2005/0251418 A1 | 11/2005 | Fox et al. | |
| 2006/0052678 A1 | 3/2006 | Drinan et al. | |
| 2006/0058593 A1 | 3/2006 | Drinan et al. | |
| 2006/0097949 A1 | 5/2006 | Luebke et al. | |
| 2006/0206013 A1 | 9/2006 | Rothman et al. | |
| 2007/0043282 A1 | 2/2007 | Mannheimer et al. | |
| 2007/0106172 A1 | 5/2007 | Abreu | |
| 2007/0179585 A1 | 8/2007 | Chandler et al. | |
| 2007/0191273 A1 | 8/2007 | Ambati et al. | |
| 2007/0213700 A1 | 9/2007 | Davison et al. | |
| 2007/0248542 A1 | 10/2007 | Kane et al. | |
| 2008/0009764 A1 | 1/2008 | Davies | |
| 2008/0015894 A1 | 1/2008 | Miller et al. | |
| 2008/0027509 A1 | 1/2008 | Andino et al. | |
| 2008/0039700 A1 | 2/2008 | Drinan et al. | |
| 2008/0048680 A1 | 2/2008 | Hargreaves et al. | |
| 2008/0259577 A1 | 10/2008 | Hu et al. | |
| 2008/0278336 A1 | 11/2008 | Ortega et al. | |
| 2009/0047694 A1 | 2/2009 | Shuber | |
| 2009/0076410 A1 | 3/2009 | Libbus et al. | |
| 2009/0104797 A1 | 4/2009 | Tseng et al. | |
| 2009/0124924 A1 | 5/2009 | Eror et al. | |

(56) References Cited

U.S. PATENT DOCUMENTS

| | | |
|---|---|---|
| 2009/0189092 A1 | 7/2009 | Aoi et al. |
| 2009/0209830 A1 | 8/2009 | Nagle et al. |
| 2009/0285785 A1 | 11/2009 | Jimi et al. |
| 2009/0326346 A1 | 12/2009 | Kracker et al. |
| 2010/0017182 A1 | 1/2010 | Voros et al. |
| 2010/0030167 A1 | 2/2010 | Thirstrup et al. |
| 2010/0042389 A1 | 2/2010 | Farruggia et al. |
| 2010/0073170 A1 | 3/2010 | Siejko et al. |
| 2010/0113979 A1 | 5/2010 | Sarrafzadeh et al. |
| 2010/0268111 A1 | 10/2010 | Drinan et al. |
| 2010/0298687 A1 | 11/2010 | Yoo et al. |
| 2010/0312233 A1 | 12/2010 | Furnish et al. |
| 2010/0324455 A1 | 12/2010 | Rangel et al. |
| 2010/0324611 A1 | 12/2010 | Deming et al. |
| 2011/0046505 A1 | 2/2011 | Cornish et al. |
| 2011/0160548 A1 | 6/2011 | Forster |
| 2011/0175844 A1 | 7/2011 | Berggren et al. |
| 2011/0184264 A1 | 7/2011 | Galasso, Jr. et al. |
| 2011/0191122 A1 | 8/2011 | Kharraz Tavakol et al. |
| 2011/0237926 A1 | 9/2011 | Jensen |
| 2011/0263950 A1 | 10/2011 | Larson et al. |
| 2011/0301441 A1 | 12/2011 | Bandic et al. |
| 2011/0313311 A1 | 12/2011 | Gaw |
| 2012/0029410 A1 | 2/2012 | Koenig et al. |
| 2012/0061257 A1 | 3/2012 | Yu et al. |
| 2012/0078088 A1 | 3/2012 | Whitestone et al. |
| 2012/0150011 A1 | 6/2012 | Besio |
| 2012/0179006 A1 | 7/2012 | Jansen et al. |
| 2012/0190989 A1 | 7/2012 | Kaiser et al. |
| 2012/0271121 A1 | 10/2012 | Della Torre et al. |
| 2013/0041235 A1 | 2/2013 | Rogers et al. |
| 2013/0072870 A1 | 3/2013 | Heppe et al. |
| 2013/0121544 A1 | 5/2013 | Sarrafzadeh et al. |
| 2013/0123587 A1 | 5/2013 | Sarrafzadeh et al. |
| 2013/0137951 A1 | 5/2013 | Chuang et al. |
| 2013/0253285 A1 | 9/2013 | Bly et al. |
| 2013/0261496 A1 | 10/2013 | Engler et al. |
| 2013/0301255 A1 | 11/2013 | Kim et al. |
| 2013/0310440 A1 | 11/2013 | Duskin et al. |
| 2013/0333094 A1 | 12/2013 | Rogers et al. |
| 2013/0338661 A1 | 12/2013 | Behnke, II |
| 2014/0121479 A1 | 5/2014 | O'Connor et al. |
| 2014/0142984 A1 | 5/2014 | Wright et al. |
| 2014/0200486 A1 | 7/2014 | Bechtel et al. |
| 2014/0221792 A1 | 8/2014 | Miller et al. |
| 2014/0273025 A1 | 9/2014 | Hurskainen et al. |
| 2014/0275823 A1 | 9/2014 | Lane et al. |
| 2014/0288397 A1 | 9/2014 | Sarrafzadeh et al. |
| 2014/0298928 A1 | 10/2014 | Duesterhoft et al. |
| 2014/0316297 A1 | 10/2014 | McCaughan et al. |
| 2014/0318699 A1 | 10/2014 | Longinotti-Buitoni et al. |
| 2015/0002168 A1 | 1/2015 | Kao et al. |
| 2015/0009168 A1 | 1/2015 | Levesque et al. |
| 2015/0094548 A1 | 4/2015 | Sabatini et al. |
| 2015/0157435 A1 | 6/2015 | Chasins et al. |
| 2015/0186607 A1 | 7/2015 | Gileijnse et al. |
| 2015/0230863 A1 | 8/2015 | Youngquist et al. |
| 2015/0343173 A1 | 12/2015 | Tobescu et al. |
| 2015/0363567 A1 | 12/2015 | Pettus |
| 2015/0366499 A1 | 12/2015 | Sarrafzadeh et al. |
| 2015/0371522 A1 | 12/2015 | Mravyan et al. |
| 2016/0015962 A1 | 1/2016 | Shokoueinejad Maragheh et al. |
| 2016/0038055 A1 | 2/2016 | Wheeler et al. |
| 2016/0058342 A1 | 3/2016 | Maiz-Aguinaga et al. |
| 2016/0072308 A1 | 3/2016 | Nyberg et al. |
| 2016/0100790 A1 | 4/2016 | Cantu et al. |
| 2016/0101282 A1 | 4/2016 | Bergelin et al. |
| 2016/0174631 A1 | 6/2016 | Tong et al. |
| 2016/0174871 A1 | 6/2016 | Sarrafzadeh et al. |
| 2016/0220172 A1 | 8/2016 | Sarrafzadeh et al. |
| 2016/0270672 A1 | 9/2016 | Chen et al. |
| 2016/0270968 A1 | 9/2016 | Stanford et al. |
| 2016/0278692 A1 | 9/2016 | Larson et al. |
| 2016/0296268 A1 | 10/2016 | Gee et al. |
| 2016/0310034 A1 | 10/2016 | Tonar et al. |
| 2016/0338591 A1 | 11/2016 | Lachenbruch et al. |
| 2017/0007153 A1 | 1/2017 | Tonar et al. |
| 2017/0014044 A1 | 1/2017 | Tonar et al. |
| 2017/0014045 A1 | 1/2017 | Tonar et al. |
| 2017/0105646 A1 | 4/2017 | Bryenton et al. |
| 2017/0156658 A1 | 6/2017 | Maharbiz et al. |
| 2017/0172489 A1 | 6/2017 | Afentakis |
| 2017/0188841 A1 | 7/2017 | Ma et al. |
| 2017/0238849 A1 | 8/2017 | Chapman et al. |
| 2017/0255812 A1 | 9/2017 | Kwon |
| 2017/0311807 A1 | 11/2017 | Fu et al. |
| 2017/0319073 A1 | 11/2017 | DiMaio et al. |
| 2018/0020058 A1 | 1/2018 | Martines et al. |
| 2018/0045725 A1 | 2/2018 | Yoo et al. |
| 2018/0220924 A1 | 8/2018 | Burns et al. |
| 2018/0220953 A1 | 8/2018 | Burns et al. |
| 2018/0220954 A1 | 8/2018 | Burns et al. |
| 2018/0220961 A1 | 8/2018 | Burns et al. |
| 2018/0360344 A1 | 12/2018 | Burns et al. |
| 2019/0000352 A1 | 1/2019 | Everett et al. |
| 2019/0038133 A1 | 2/2019 | Tran |
| 2019/0053751 A1 | 2/2019 | Torres |
| 2019/0060602 A1 | 2/2019 | Tran et al. |
| 2019/0069836 A1 | 3/2019 | Hettrick |
| 2019/0104981 A1 | 4/2019 | Sarrafzadeh et al. |
| 2019/0104982 A1 | 4/2019 | Dunn et al. |
| 2019/0117964 A1 | 4/2019 | Bahrami et al. |
| 2019/0134396 A1 | 5/2019 | Toth et al. |
| 2019/0142333 A1 | 5/2019 | Burns et al. |
| 2019/0147990 A1 | 5/2019 | Burns et al. |
| 2019/0148901 A1 | 5/2019 | Komoto |
| 2019/0150882 A1 | 5/2019 | Maharbiz et al. |
| 2019/0175098 A1 | 6/2019 | Burns et al. |
| 2019/0192066 A1 | 6/2019 | Schoess et al. |
| 2019/0246972 A1 | 8/2019 | Burns et al. |
| 2019/0282436 A1 | 9/2019 | Douglas et al. |
| 2019/0290189 A1 | 9/2019 | Sarrafzadeh et al. |
| 2019/0307360 A1 | 10/2019 | Tonar et al. |
| 2019/0307405 A1 | 10/2019 | Terry et al. |
| 2020/0008299 A1 | 1/2020 | Tran et al. |
| 2020/0043607 A1 | 2/2020 | Zerhusen et al. |
| 2020/0069240 A1 | 3/2020 | Burns |
| 2020/0069241 A1 | 3/2020 | Burns |
| 2020/0069242 A1 | 3/2020 | Burns et al. |
| 2020/0077892 A1 | 3/2020 | Tran |
| 2020/0078499 A1 | 3/2020 | Gadde et al. |
| 2020/0093395 A1 | 3/2020 | Tonar et al. |
| 2020/0100723 A1 | 4/2020 | Burns |
| 2020/0113488 A1 | 4/2020 | Al-Ali et al. |
| 2020/0127398 A1 | 4/2020 | Burns et al. |
| 2020/0296821 A1 | 9/2020 | Trublowski et al. |
| 2020/0297244 A1 | 9/2020 | Brownhill et al. |
| 2020/0297255 A1 | 9/2020 | Martinez et al. |
| 2022/0287584 A1 | 9/2022 | Burns et al. |

FOREIGN PATENT DOCUMENTS

| | | |
|---|---|---|
| CA | 2609842 C | 10/2016 |
| CN | 204119175 U | 1/2015 |
| CN | 104352230 A | 2/2015 |
| CN | 104567657 A | 4/2015 |
| CN | 105578333 A | 5/2016 |
| CN | 105963074 A | 9/2016 |
| CN | 208111467 U | 11/2018 |
| DE | 102012011212 A1 | 12/2012 |
| EP | 1080687 A1 | 3/2001 |
| EP | 1372475 B1 | 1/2004 |
| EP | 1569553 A1 | 9/2005 |
| EP | 3092946 A1 | 11/2016 |
| EP | 3280488 B1 | 12/2018 |
| GB | 2584808 A | 12/2020 |
| JP | 2000-060805 A | 2/2000 |
| JP | 2001-178705 | 7/2001 |
| JP | 2001-326773 A | 11/2001 |
| JP | 2003-169788 A | 6/2003 |
| JP | 2003-290166 A | 10/2003 |
| JP | 2005-52227 | 3/2005 |
| JP | 2009-268611 A | 11/2009 |
| JP | 4418419 | 2/2010 |

(56) References Cited

FOREIGN PATENT DOCUMENTS

| | | |
|---|---|---|
| JP | 2013-198639 A | 10/2013 |
| KR | 10-2014-0058445 | 5/2014 |
| WO | 1996/010951 A1 | 4/1996 |
| WO | 2001/054580 A1 | 8/2001 |
| WO | 2002/080770 A1 | 10/2002 |
| WO | 2004/105602 A1 | 12/2004 |
| WO | 2006/029035 A1 | 3/2006 |
| WO | 2007/098762 A1 | 9/2007 |
| WO | 2009/144615 A1 | 12/2009 |
| WO | 2010/060102 A2 | 5/2010 |
| WO | 2011/004165 A1 | 1/2011 |
| WO | 2011/022418 A2 | 2/2011 |
| WO | 2011/080080 A1 | 7/2011 |
| WO | 2011/080262 A1 | 7/2011 |
| WO | 2011/091517 A1 | 8/2011 |
| WO | 2011/143071 A2 | 11/2011 |
| WO | 2013/116242 A2 | 8/2013 |
| WO | 2014/186894 A1 | 11/2014 |
| WO | 2015/003015 A2 | 1/2015 |
| WO | 2015/022583 A2 | 2/2015 |
| WO | 2015/077838 A1 | 6/2015 |
| WO | 2015/168720 A1 | 11/2015 |
| WO | 2015/169911 A1 | 11/2015 |
| WO | 2015/195720 A1 | 12/2015 |
| WO | 2016/098062 A1 | 6/2016 |
| WO | 2016/172263 A1 | 10/2016 |
| WO | 2016/172264 A1 | 10/2016 |
| WO | 2017/032393 | 3/2017 |
| WO | 2017/214188 A1 | 12/2017 |
| WO | 2017/218818 A2 | 12/2017 |
| WO | 2018/071715 A1 | 4/2018 |
| WO | 2018/077560 A1 | 5/2018 |
| WO | 2018/115461 A1 | 6/2018 |
| WO | 2018/144938 | 8/2018 |
| WO | 2018/144941 | 8/2018 |
| WO | 2018/144943 | 8/2018 |
| WO | 2018/144946 | 8/2018 |
| WO | WO-2018168424 A1 * 9/2018 ........... G01D 11/245 | |
| WO | 2018/189265 A1 | 10/2018 |
| WO | 2018/209100 A1 | 11/2018 |
| WO | 2018/234443 A1 | 12/2018 |
| WO | 2018/236739 | 12/2018 |
| WO | 2019/020551 A1 | 1/2019 |
| WO | 2019/030384 A2 | 2/2019 |
| WO | 2019/048624 A1 | 3/2019 |
| WO | 2019/048626 A1 | 3/2019 |
| WO | 2019/048638 A1 | 3/2019 |
| WO | 2019/072531 A1 | 4/2019 |
| WO | 2019/073389 A1 | 4/2019 |
| WO | 2019/076967 A2 | 4/2019 |
| WO | 2019/096828 A1 | 5/2019 |
| WO | 2019/099810 A1 | 5/2019 |
| WO | 2019/099812 A1 | 5/2019 |
| WO | 2019/113481 | 6/2019 |
| WO | 2019/157290 | 8/2019 |
| WO | 2019/162272 A1 | 8/2019 |
| WO | 2020/014779 A1 | 1/2020 |
| WO | 2020/043806 A1 | 3/2020 |
| WO | 2020/053290 A1 | 3/2020 |
| WO | 2020/077100 A1 | 4/2020 |
| WO | 2020/187643 A1 | 9/2020 |
| WO | 2020/187851 A1 | 9/2020 |
| WO | 2020/234429 A2 | 11/2020 |

OTHER PUBLICATIONS

Alanen, "Measurement of Hydration in the Stratum Corneum with the MoistureMeter and Comparison with the Corneometer," *Skin Research and Technology*, 10:32-37 (2004).

Alberts et al., "The Extracellular Matrix of Animals," Molecular Biology of the Cell, 4th ed., pp. 1065-1127 (2002).

Allman et al., "Pressure Ulcer Risk Factors Among Hospitalized Patients with Activity Limitation," *JAMA*, 273:865-870 (1995).

Anonymous, "Recommended Practices for Positioning the Patient in the Perioperative Practice Setting," in *Perioperative Standards, Recommended Practices, and Guidelines*, AORN, Inc., 525-548 (2006).

Arao et al., "Morphological Characteristics of the Dermal Papillae in the Development of Pressure Sores," *World Wide Wounds* (Mar. 1999), 6 pages (obtained online).

Australian Intellectual Property Office, Office Action dated May 1, 2014, for corresponding Australian patent application No. 2011253253 (pp. 1-10) and pending claims (pp. 11-15) pp. 1-15.

Australian Patent Office, Office Action dated Jun. 1, 2015, for corresponding Australian Patent Application No. 2011253253 (pp. 1-4) and claims (pp. 5-10) pp. 1-10.

Bader et al., "Effect of Externally Applied Skin Surface Forces on Tissue Vasculature," *Archives of Physical Medicine and Rehabilitation*, 67(11):807-11 (1986).

Barnes, "Moisture Meters for Use on Thin Lumber and Veneers," *Moisture Register Co.*, 1-5 (1956).

Bates-Jensen et al., "Subepidermal Moisture Predicts Erythema and Stage 1 Pressure Ulcers in Nursing Home Residents: A Pilot Study," Journal of the American Geriatric Society, 55:1199-1205 (2007).

Bates-Jensen et al., "subepidermal moisture differentiates erythema and stage 1 pressure ulcers in nursing home residents," Wound Repair Regeneration, 16:189-197 (2008).

Bates-Jensen et al., "Subepidermal Moisture Is Associated with Early Pressure Ulcer Damage in Nursing Home Residents with Dark Skin Tones; Pilot Findings," Journal of Wound Ostomy and Continence Nursing, 36(3):277-284 (2009).

Bates-Jensen et al., "Subepidermal Moisture Detection of Pressure Induced Tissue Damage on the Trunk: The Pressure Ulcer Detection Study Outcomes," Wound Repair and Regeneration, 25:502-511 (2017).

Berggren, "Capacitive Biosensors," Electroanalysis, 13(3):173-180 (2001), Wiley-VCH (publisher), Weinheim, Germany.

Bergstrand et al., "Pressure-induced Vasodilation and Reactive Hyperemia at Different Depths in Sacral Tissue Under Clinically Relevant Conditions," Microcirculation, 21:761-771 (2014).

Bergstrom et al., "Pressure Ulcers in Adults: Prediction and Prevention," Clinical Practice Guideline—Quick Reference Guide for Clinicians, 117 (1992).

Black et al., "Differential Diagnosis of Suspected Deep Tissue Injury," *International Wound Journal*, 13(4):531-539 (2015).

Brem et al., "Protocol for the Successful Treatment of Pressure Ulcers," *The American Journal of Surgery*, 188 (Suppl. To Jul. 2004):9S-17S (2004).

Brem et al. "High cost of stage IV pressure ulcers," American Journal of Surgery, 200:473-477 (2010).

Brienza et al., "Friction-Induced Skin Injuries—Are They Pressure Ulcers?," Journal of Wound Ostomy and Continence Nursing, 42(1):62-64 (2015).

Carmo-Araujo et al., "Ischaemia and reperfusion effects on skeletal muscle tissue: morphological and histochemical studies," International Journal of Experimental Pathology, 88:147-154 (2007).

Ceelen et al., "Compression-induced damage and internal tissue strains are related," Journal of Biomechanics, 41:3399-3404 (2008).

Ching et al., "Tissue electrical properties monitoring for the prevention of pressure sore," Prosthetics and Orthotics International, 35(4):386-394 (2011).

Clendenin et al., "Inter-operator and inter-device agreement and reliability of the SEM Scanner," Journal of Tissue Viability, 24(1):17-23 (2015).

De Lorenzo et al., "Predicting body cell mass with bioimpedance by using theoretical methods: a technological review," Journal of Applied Physiology, 82(5):1542-1558 (1997).

De Oliveira et al., "Sub-epidermal moisture versus tradition and visual skin assessments to assess pressure ulcer risk in surgery patients," Journal of Wound Care, 31(3):254-264 (2022), Mark Allen Group (pub.) (obtained online).

Demarre et al., "The cost of pressure ulcer prevention and treatment in hospitals and nursing homes in Flanders: A cost-of-illness study," International Journal of Nursing Studies, 1-14 (2015).

Dodde et al., "Bioimpedance of soft tissue under compression," Physiology Measurement, 33(6):1095-1109 (2012).

(56) References Cited

OTHER PUBLICATIONS

Dupont, "Pyralux® FR Coverlay, Bondply & Sheet Adhesive," webpage, Retrieved from: www2.dupont.com/Pyralux/en_US/products/adhesives_films/FR/FR_films_html pp. 1-2 (2012).
DuPont, "General Specifications for Kapton Polyimide Film," Retrieved from Dupont: http://www2.dupont.com/Kapton/en_US/assets/downloads/pdf/Gen_Specs.pdf, pp. 1-7 (2012).
DuPont, "Pyralux® FR Copper-clad Laminate," webpage, Retrieved from: www2.dupont.com/Pyraluxlen_US/ productsllaminate/FR/pyralux_fr.html, pp. 1-2 (2012).
Eberlein-Gonska et al., "The Incidence and Determinants of Decubitus Ulcers in Hospital Care: An Analysis of Routine Quality Management Data at a University Hospital," Deutsches Arzteblatt International, 110(33-34):550-556 (2013).
European Patent Office, ESSR issued on Aug. 22, 2014, for corresponding European Patent Application No. 11781061.4 (pp. 1-7) and pending claims (pp. 3-10) pp. 1-10.
European Patent Office, Office Action dated Jul. 13, 2015, for corresponding European Patent Application No. 11781061.4 (pp. 1-5) and claims (pp. 6-9) pp. 1-9.
Extended European Search Report dated Aug. 30, 2016, in European Patent Application No. 16169670.
Extended European Search Report dated Oct. 18, 2016, in European Patent Application No. 16166483.4.
Extended European Search Report dated Mar. 13, 2017, in European Patent Application No. 16196899.5.
Extended European Search Report dated Oct. 25, 2019, in European Patent Application No. 19186393.5.
Extended European Search Report dated Nov. 19, 2019, in European Patent Application No. 19190000.0.
Extended European Search Report dated Feb. 6, 2020, in European Patent Application No. 18748733.5.
Extended European Search Report dated Feb. 10, 2020, in European Patent Application No. 18748025.6.
Extended European Search Report dated Feb. 10, 2020, in European Patent Application No. 18748512.3.
Extended European Search Report dated Jun. 24, 2020, in European Patent Application No. 18747707.0.
Extended European Search Report dated Mar. 17, 2022, in European Patent Application No. 19838240.0.
Extended European Search Report dated May 24, 2022, in European Patent Application No. 19871332.3.
Ford, "Hospice Wins Award for Innovation in Pressure Ulcer Prevention," *Nursing Times*, downloaded and printed on Apr. 18, 2020, from https://www.nursingtimes.net/news/research-and-innovation/hospice-wins-award-for-innovation-in-pressure-ulcer-prevention-30-11-2018/ (2018).
Gabriel et al., "The dielectric properties of bilogical tissues: II. Measurements in the frequency range 10 Hz to 20 GHz," Physics in Medicine and Biology, 41:2251-69 (1996).
Gabriel, "Compilation of the Dielectric Properties of Body Tissues at Rf and Microwave Frequencies Report," Occupational and Environmental Health Directorate, (1996).
Gardiner et al., "Incidence of hospital-acquired pressure ulcers—a population-based cohort study," International Wound Journal, 11(6):696-700 (2014).
Gershon et al., "SEM Scanner Readings to Assess Pressure Induced Tissue Damage," Proceedings of the 17th Annual European Pressure Ulcer Advisory Panel (EPUAP) meeting, Stockholm, Sweden (2014).
Gonzalez-Correa et al., "Electrical bioimpedance readings increase with higher pressure applied to the measuring probe," Physiology Measurement, 26:S39-S47 (2005).
Great Britain Search Report dated Apr. 27, 2020, in Great Britain Patent Application No. GB2002889.0.
Great Britain Search Report dated Jun. 28, 2021, in Great Britain Patent Application No. GB2106848.1.
Great Britain Search Report dated Feb. 9, 2022, in Great Britain Patent Application No. GB2118088.0.
Great Britain Search Report dated Feb. 14, 2022, in Great Britain Patent Application No. GB2118092.2.
Guihan et al., "Assessing the feasibility of subepidermal moisture to predict erythema and stage 1 pressure ulcers in persons with spinal cord injury: A pilot study," Journal of Spinal Cord Medicine, 35(1):46-52 (2012).
Hamazoto et al., "Estimate of Burn Depth by Non-Invasive Capacitance Measurement," *Japan Soc. ME & BE*, 42:266 (Jun. 2003).
Harrow, "Subepidermal moisture surrounding pressure ulcers in persons with a spinal cord injury: A pilot study," Journal of Spinal Cord Medicine, 37(6):719-728 (2014).
Hou, "Section IV. Osteofascial Compartment Syndrome," Limbs Trauma, 7:215-217 (2016), Hubei Science & Technology Publishing House (pub.), Wuhan, China.
Houwing et al., "Pressure-induced skin lesions in pigs: reperfusion injury and the effects of vitamin E," Journal of Wound Care, 9(1):36-40 (2000).
Huang et al., "A device for skin moisture and environment humidity detection," Sensors and Actuators B: Chemical, 206-212 (2008).
International Search Report and Written Opinion dated Feb. 9, 2012, for International Patent Application No. PCT/US2011/035618.
International Search Report and Written Opinion dated Jul. 22, 2016, for International Patent Application No. PCT/US2016/28515.
International Search Report and Written Opinion dated Jul. 26, 2016, for International Patent Application No. PCT/US2016/28516.
International Search Report dated Apr. 12, 2018, issued in International Patent Application No. PCT/US2018/016731.
International Search Report dated Apr. 12, 2018, issued in International Patent Application No. PCT/US2018/016738.
International Search Report dated Apr. 26, 2018, issued in International Patent Application No. PCT/US2018/016741.
International Search Report dated Jul. 12, 2018, issued in International Patent Application No. PCT/US2018/016736.
International Search Report dated Sep. 10, 2018, issued in International Patent Application No. PCT/US2018/038055.
International Search Report dated Jan. 29, 2019, issued in International Patent Application No. PCT/US2018/061494.
International Search Report dated Feb. 5, 2019, issued in International Patent Application No. PCT/US2018/064527.
International Search Report dated Feb. 11, 2019, issued in International Patent Application No. PCT/US2018/061497.
International Search Report dated May 29, 2019, issued in International Patent Application No. PCT/US2019/017226.
International Search Report dated Mar. 9, 2020, issued in International Patent Application No. PCT/US2019/055655.
International Search Report dated Dec. 8, 2020, issued in International Patent Application No. PCT/US2020/051134.
International Search Report dated Aug. 17, 2021, issued in International Patent Application No. PCT/US2021/023818.
International Search Report dated May 13, 2022, issued in International Patent Application No. PCT/US2022/014913.
International Search Report dated Aug. 2, 2022, issued in International Patent Application No. PCT/US2022/025508.
International Search Report dated Aug. 15, 2022, issued in International Patent Application No. PCT/US2022/019338.
Jan et al., "Local cooling reduces skin ischemia under surface pressure in rats: an assessment by wavelet analysis of laser Doppler blood flow oscillations," Physiology Measurement, 33(10):1733-1745 (2012).
Jaskowski, "Evaluation of the Healing Process of Skin Wounds by Means of Skin Absolute Value of Electrical Impedance," *Dermatol. Mon.schr.*, 172(4):223-228 (1986).
Jiang et al., "Ischemia-Reperfusion Injury-Induced Histological Changes Affecting Early Stage Pressure Ulcer Development in a Rat model," Ostomy Wound Management, 57:55-60 (2011).
Jiang et al., "Expression of cytokines, growth factors and apoptosis-related signal molecules in chronic pressure ulcer wounds healing," Spinal Cord, 52(2):145-151 (2014).
Jiricka et al., "Pressure Ulcer Risk factors in an ICU Population," American Journal of Critical Care, 4:361-367 (1995).
Kanai et al., "Electrical measurement of fluid distribution in legs and arms," Medical Progress through Technology Journal, 12:159-170 (1987).

(56) References Cited

OTHER PUBLICATIONS

Kasuya et al., "Potential application of in vivo imaging of impaired lymphatic duct to evaluate the severity of pressure ulcer in mouse model," Scientific Reports, 4:4173 (7 pages) (2014).
Lee, "CapSense Best Practices," Application Note 2394, 1-10 (2007).
Liu et al., "A Systematic Review of Electrical Stimulation for Pressure Ulcer Prevention and Treatment in People with Spinal Cord Injuries," The Journal of Spinal Cord Medicine, 37(6):703-718 (2014).
Loerakker et al., "Temporal Effects of Mechanical Loading on Deformation-Induced Damage in Skeletal Muscle Tissue," Annual Review of Biomedical Engineering, 38(8):2577-2587 (2010).
Loerakker et al., "The effects of deformation, ischemia, and reperfusion on the development of muscle damage during prolonged loading," Journal of Applied Physiology, 111(4):1168-1177 (2011).
Lyder et al., "Quality of Care for Hospitalized Medicare Patients at Risk for Pressure Ulcers," Archives of Internal Medicine,161:1549-1554 (2001).
Martinsen, "Bioimpedance and Bioelectricity Basics," Elsevier Academic Press, Chapters 1 and 10 (2015).
Mathiesen et al., "Are labour-intensive efforts to prevent pressure ulcers cost-effective?" Journal of Medical Economics, 16(10):1238-1245 (2013).
Matthie et al., "Analytic assessment of the various bioimpedance methods used to estimate body water," Journal of Applied Physiology, 84(5):1801-1816 (1998).
Miller et al., "Lymphatic Clearance during Compressive Loading," Lymphology, 14(4):161-166 (1981).
Moore et al., "A randomised controlled clinical trial of repositioning, using the 30° tilt, for the prevention of pressure ulcers," Journal of Clinical Nursing, 20:2633-2644 (2011).
Moore et al., "Pressure ulcer prevalence and prevention practices in care of the older person in the Republic of Ireland," Journal of Clinical Nursing, 21:362-371 (2012).
Moore et al., "A review of PU prevalence and incidence across Scandinavia, Iceland and Ireland (Part I)", Journal of Wound Care, 22(7):361-362, 364-368 (2013).
Moore et al., "Subepidermal Moisture (SEM) and Bioimpedance: A Literature Review of a Novel Method for Early Detection of Pressure-Induced Tissue Damage (Pressure Ulcers)," International Wound Journal, 14(2):331-337 (2016).
Moore, "Using SEM (Sub Epidermal Moisture) Measurement for Early Pressure Ulcer Detection," Institute for Pressure Injury Prevention, WCICT 2017 (Jun. 20-21), Manchester, UK, 7 pp., available at www.pressureinjuryprevention.com/wp-content/uploads/2017/07/ipip_Moore_Sub_Epidermal_Moisture_notes.pdf (2017) (obtained online).
Moore et al., "SEM Scanner Made Easy," Wounds International, pp. 1-6, available at www.woundsinternational.com (2018).
Mulasi, "Bioimpedance at the Bedside: Current Applications, Limitations, and Opportunities," Nutritional Clinical Practice, 30(2):180-193 (2015).
Musa et al., "Clinical impact of a sub-epidermal moisture scanner: what is the real-world use?," J. Wound Care, 30(3):2-11 (2021), Mark Allen Group (pub.) (obtained online).
National Pressure Ulcer Advisory Panel et al., "Prevention and Treatment of Pressure Ulcers: Clinical Practice Guideline," Cambridge Media, (2014).
Nixon et al., "Pathology, diagnosis, and classification of pressure ulcers: comparing clinical and imaging techniques," Wound Repair and Regeneration, 13(4):365-372 (2005).
Nuutinen et al., "Validation of a new dielectric device to assess changes of tissue water in skin and subcutaneous fat," Physiological Measurement, 25:447-454 (2004).
O'Goshi, "Skin conductance; validation of Skicon-200EX compared to the original model, Skicon-100," Skin Research and Technology, 13:13-18 (2007).
Oliveira, "The Accuracy of Ultrasound, Thermography, Photography and Sub-Epidermal Moisture as a Predictor of Pressure Ulcer Presence—a Systematic Review," RCSI, School of Nursing thesis (2015).
Oomens et al., "Pressure Induced Deep Tissue Injury Explained," Annual Review of Biomedical Engineering, 43(2):297-305 (2015).
Pang et al. (eds.) Diagnosis and Treatment of Diabetes, China Press of Traditional Chinese Medicine (publisher), Beijing, China, pp. 466-468 (Oct. 2016), with English Translation.
Rotaru et al., "Friction between Human Skin and Medical Textiles for Decubitus Prevention," Tribology International, 65:91-96 (2013).
Saxena, The Pocket Doctor: Obstetrics & Gynecology, pp. 76-77 (2017), Tianjin Science & Technology Translation & Publishing Co. Ltd. (pub.), Tianjin, China.
Scallan et al., "Chapter 4: Pathophysiology of Edema Formation," Capillary Fluid Exchange: Regulation, Functions, and Pathology, 47-61 (2010).
Schultz et al., "Extracellular matrix: review of its role in acute and chronic wounds," World Wide Wounds, 1-20 (2005).
Schwan, "Electrical properties of tissues and cells," Advances in Biology and Medical Physics, 15:148-199 (1957).
Seibert et al., "Technical Expert Panel Summary Report: Refinement of a Cross-Setting Pressure Ulcer/Injury Quality Measure for Skilled Nursing Facilities, Inpatient Rehabilitation Facilities, Long-Term Care Hospitals, and Home Health Agencies," RTI International Abt Associates, CMS Contract No. HHSM-500-2013-130151, 49 pp. (Aug. 2019).
Sener et al., "Pressure ulcer-induced oxiadative organ injury is ameliorated by beta-glucan treatment in rats," International Immunopharmacology, 6(5):724-732 (2006).
Sewchuck et al., "Prevention and Early Detection of Pressure Ulcers in Patients Undergoing Cardian Surgery," AORN Journal, 84(1):75-96 (2006).
Sprigle et al., "Analysis of Localized Erythema Using Clinical Indicators and Spectroscopy," Ostomy Wound Management, 49:42-52 (2003).
Stekelenburg et al., "Role of ischemia and deformation in the onset of compression-induced deep tissue injury: MRI-based studies in a rat model," Journal of Applied Physiology, 102:2002-2011 (2007).
Stekelenburg et al., "Deep Tissue Injury: How Deep is Our Understanding?" Archives of Physical Medicine Rehabilitation, 89(7):1410-1413 (2008).
Supplementary Partial European Search Report dated Jan. 27, 2020, in European Patent Application No. 18747707.
Supplementary Partial European Search Report dated Jul. 13, 2021, in European Patent Application No. 18887039.
Supplementary Partial European Search Report dated Oct. 1, 2021, in European Patent Application No. 19751130.
Swisher et al., "Impedance sensing device enables early detection of pressure ulcers in vivo," Nature Communications, 6:6575-6584 (2015).
Thomas et al., "Hospital-Acquired Pressure Ulcers and Risk of Death," Journal of the American Geriatrics Society, 44:1435-1440 (1996).
Thomas, "Prevention and Treatment of Pressure Ulcers," J. Am. Med. Dir. Assoc., 7:46-59 (2006).
Truong et al., "Pressure Ulcer Prevention in the Hospital Setting Using Silicone Foam Dressings," Cureus, 8(8):e730, pp. 1-6 (2016).
Tur et al., "Topical Hydrogen Peroxide Treatment of Ischemic Ulcers in the Guinea Pig: Blood Recruitment in Multiple Skin Sites," J. Am. Acad. Dermatol., 33:217-221 (1995).
Valentinuzzi et al., "Bioelectrical Impedance Techniques in Medicine. Part II: Monitoring of Physiological Events by Impedance," Critical Reviews in Biomedical Engineering, 24(4-6):353-466 (1996).
Vangilder et al., "Results of Nine International Pressure Ulcer Prevalence Surveys: 1989 to 2005," Ostomy Wound Management, 54(2):40-54 (2008).
Vowden et al., "Diabetic Foot Ulcer or Pressure Ulcer? That Is the Question," The Diabetic Foot Journal, 18:62-66 (2015).
Wagner et al., "Bioelectrical Impedance as a Discriminator of Pressure Ulcer Risk," Advances in Wound Care, 9(2):30-37 (1996).

(56) References Cited

OTHER PUBLICATIONS

Wang et al., "A Wireless Biomedical Instrument for Evidence-Based Tissue Wound Characterization," *Wireless Health*, pp. 222-223 (2010).
Wang, "Biomedical Systen for Monitoring Pressure Ulcer Development," UCLA Electronic Theses and Dissertations, California, USA, pp. 1-123 (2013).
Watanabe et al., "CT anlysis of the use of the electrical impedance technique to estimate local oedema in the extremities in patients with lymphatic obstruction," Medical and Biological Engineering and Computing, 36(1):60-65 (1998).
Weiss, "Tissue destruction by neutrophils," The New England Journal of Medicine, 320(6):365-76 (1989).
Yang, *Handbook of Practical Burn Surgery*, p. 48 (2008), People's Military Medical Press (pub.), Beijing, China.
Zanibbi, "Pattern Recognition: An Overview," downloaded from https://www.cs.rit.edu/~rlaz/prec20092/slides/Overview.pdf, 30 pp. (2010).

* cited by examiner

DEVICE WITH DISPOSABLE ELEMENT

CROSS REFERENCE TO RELATED APPLICATIONS

This application is a continuation of U.S. application Ser. No. 17/751,082 filed May 23, 2022 know U.S. Pat. No. 11,600,939), which is a continuation of U.S. application Ser. No. 17/164,706 filed Feb. 1, 2021 (now U.S. Pat. No. 11,342,696), which is a continuation of U.S. application Ser. No. 16/598,758 filed Oct. 10, 2019 (now U.S. Pat. No. 10,950,960), which claims the benefit of priority of U.S. Provisional Application No. 62/744,513, filed Oct. 11, 2018, and U.S. Provisional Application No. 62/804,095, filed Feb. 11, 2019, the contents of each of which are herein incorporated by reference in their entireties and for all purposes.

FIELD

The present disclosure provides apparatus and methods for a device for detecting tissue damage through measurement of Sub-Epidermal Moisture (SEM). The present disclosure further provides apparatus and methods for a device for detecting tissue damage through measurement of SEM, where the device includes a printed circuit board (PCB) assembled into a molded frame.

BACKGROUND

A printed circuit board (PCB) is employed in medical devices as a flat base that physically supports and electronically connects electronic components and conductors. PCBs may be single-sided, double-sided, and multilayered. PCBs are currently retained in device frames by either adhesive or provision of a lip in the frame that captures the edge of the PCB.

SUMMARY

In an aspect, the present disclosure provides for, and includes, a detachable element for use with a reusable component having a retention groove and an alignment guide and a planar contact surface parallel to the retention groove, the detachable element comprising: a body comprising a retention feature configured to engage the retention groove, and an electrical contactor coupled to the body, where the contactor comprises a cantilever element that is configured to touch the planar contact surface when the retention feature is engaged with the retention groove, where the cantilever element is configured to slide along the contact surface as the detachable element is brought together with the reusable component.

In an aspect, the present disclosure provides for, and includes, a connector comprising: a reusable component comprising a retention groove and an electrical contact surface that is parallel to the retention groove; and a detachable element comprising a body with a retention feature configured to engage the retention groove and an electrical contactor coupled to the body, where the contactor comprises a compliant element that is configured to touch the contact surface of the reusable element when the retention feature of the detachable element is engaged with the retention groove of the reusable component and to slide along the contact surface as the detachable element is brought together with the reusable component.

In an aspect, the present disclosure provides for, and includes, a detachable element comprising: a body comprising a hole and a retention pocket, where the retention pocket comprises a reference surface; and a printed circuit board assembly (PCBA) comprising a printed circuit board (PCB) having an outer edge and a contactor coupled to the PCB, where a portion of the contactor extends beyond the outer edge of the PCB, where the portion of the contactor that extends beyond the outer edge of the PCB is in contact with the reference surface. In an aspect, an external surface of a PCB is flush with a surface of a frame without a protruding lip or the use of adhesive.

In an aspect, the present disclosure provides for, and includes, a detachable element comprising: a body comprising upper and lower sections joined by a flexible arm, where the upper section comprises an opening and the lower section is attached on its underside to a compressible spring; and a printed film having tabbed and non-tabbed areas, where the tabbed area comprises a sensor comprising two electrodes on one first face, and where the tabbed area is inserted between the upper and lower sections so that the sensor is aligned with the opening.

BRIEF DESCRIPTION OF THE DRAWINGS

Aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

DETAILED DESCRIPTION

Figure 1A:
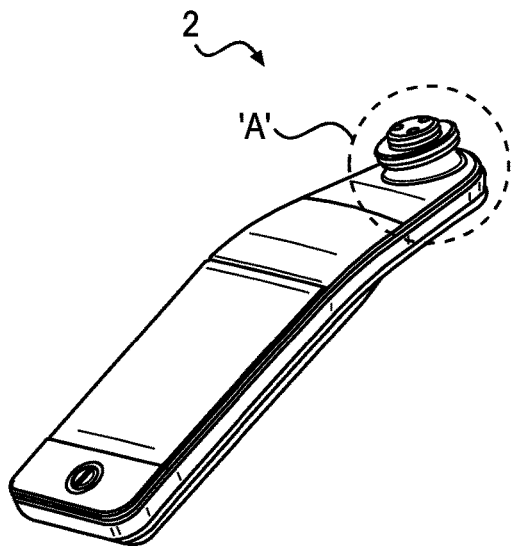
FIG. 1A depicts a medical scanner, in accordance with the present disclosure.

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that, in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations, and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only and is not intended to be limiting of the disclosure.

All publications, patent applications, patents, and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

U.S. patent application Ser. No. 14/827,375 ("the '375 application") discloses an apparatus that measures the sub-epidermal capacitance using a bipolar sensor, where the sub-epidermal capacitance corresponds to the moisture content of the target region of skin of a patient. The '375 application also discloses an array of these bipolar sensors of various sizes.

U.S. patent application Ser. No. 15/134,110 discloses an apparatus for measuring sub-epidermal moisture (SEM), where the device emits and receives an RF signal at a frequency of 32 kHz through a single coaxial sensor and generates a bioimpedance signal, then converts a biocapacitance signal to a SEM value.

U.S. patent application Ser. No. 13/942,649 discloses a compact perfusion scanner and method of characterizing tissue heath status incorporating optical sensors to monitor tissue blood perfusion measurements and oximetry.

U.S. patent application Ser. Nos. 14/827,375, 15/134,110, and 13/942,649 are incorporated herein by reference in their entireties.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein include and comprise one or more steps or actions for achieving the described method. The method steps and/or actions may be interchanged with one another without departing from the scope of the present disclosure. In other words, unless a specific order of steps or actions is required for proper operation of the embodiment, the order and/or use of specific steps and/or actions may be modified without departing from the scope of the present disclosure.

As used in the description of the disclosure and the appended claims, the singular forms "a," "an," and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a SEM value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "sub-epidermal moisture" or "SEM" refers to the increase in tissue fluid and local edema caused by vascular leakiness and other changes that modify the underlying structure of the damaged tissue in the presence of continued pressure on tissue, apoptosis, necrosis, and the inflammatory process.

As used herein, the term "biocapacitance" refers to the physical property that reflects the relative dielectric permittivity of the tissue, i.e. how much resistance to electrical fields is encountered in tissues.

As used herein, a "patient" may be a human or animal subject.

As used herein, the term "parallel" describes configurations where best-fit lines or planes of two objects have an approximately constant separation over a distance meaningful to the application. In certain embodiments, these best-fit lines or planes may have an included angle of ±1 degree, ±5 degrees, or ±10 degrees.

As used herein, the term "planar" describes configurations where the actual surface of an object varies from a best-fit ideal plane by a distance that is not significant in the function of the object. In certain embodiments, the distance between the actual surface and the ideal plane may be 0.254 mm (0.010 inches), 1.27 mm (0.050 inches), or 2.54 mm (0.100 inches).

As used herein, the term "diameter" refers to the length of a straight line segment that passes through the center of a circle and whose endpoints lie on the circle. The diameter is equal to twice the radius of the circle.

As used herein, the term "toroid" refers to a circular surface of revolution with a hole or an opening in its center.

As used herein, the term "concentric" refers to two or more objects having the same center or axis.

As used herein, the term "printed film" refers to a segment of a polymeric film upon which conductive elements have been printed.

As used herein, the term "pogo pin" refers to a spring-loaded electrical connector mechanism.

FIG. 1A depicts a medical scanner 2, in accordance with the present disclosure. In an aspect, medical scanner 2 is an SEM scanner. In an aspect, medical scanner 2 is an SEM scanner that measures biocapacitance. In an aspect, the nose of the device, indicated by the dashed line circle 'A,' is pressed against the skin of a patient to make an SEM measurement. In an aspect, the nose of the device, indicated by the dashed line circle 'A,' is pressed against the skin of a patient to make a biocapacitance measurement.

Figure 1B:
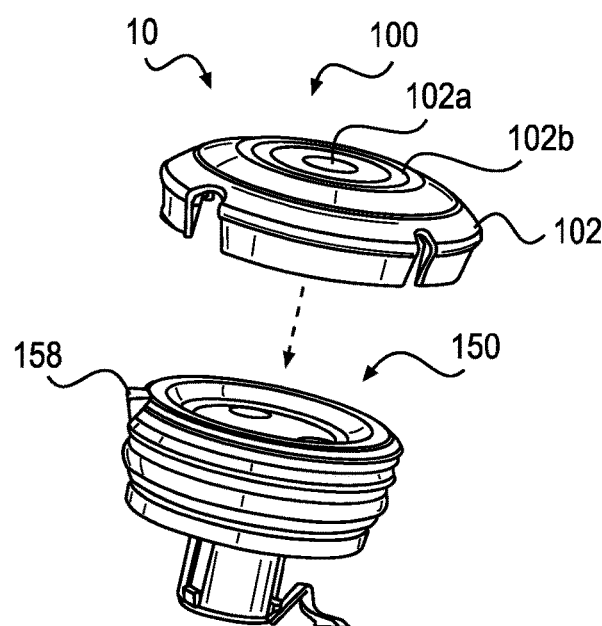
FIG. 1B depicts a connector comprising a reusable component, which is part of the medical scanner of FIG. 1A in the region "A," and a detachable element, in accordance with the present disclosure.

FIG. 1B depicts a connector 10 comprising a reusable component 150, which is part of the medical scanner of FIG. 1A in the region 'A,' and a detachable element 100, in accordance with the present disclosure. In an aspect, detachable element 100 comprises a body 102 and a sensor formed from a center electrode 102a and a toroidal electrode 102b, where center electrode 102a and toroidal electrode 102b are concentric with respect to one another. Center electrode 102a has an outer-facing surface (visible in FIG. 1B) and an inner-facing surface (not visible in FIG. 1B). Similarly, toroidal electrode 102b has an outer-facing surface (visible in FIG. 1B) and an inner-facing surface (not visible in FIG. 1B).

In an aspect, detachable element 100 comprises a sensor formed from a plurality of electrodes such as up to two electrodes, up to three electrodes, up to four electrodes, up to five electrodes, up to six electrodes, up to seven electrodes, up to eight electrodes, up to nine electrodes, up to ten electrodes, up to eleven electrodes, or up to twelve electrodes. In an aspect, detachable element 100 comprises a plurality of sensors formed from a plurality of electrodes, where each sensor is formed from up to twelve electrodes, such as up to two electrodes, up to three electrodes, up to four electrodes, up to five electrodes, up to six electrodes, up to seven electrodes, up to eight electrodes, up to nine electrodes, up to ten electrodes, or up to eleven electrodes. In an aspect, a sensor is formed from an annular ring disposed around an inner circular electrode. In an aspect, a sensor is formed from two parallel bar electrodes. In an aspect, a sensor is formed from electrodes in the form of interdigitating fingers. In an aspect, detachable element 100 comprises a body 102 and a plurality of sensors selected from the group consisting of a plurality of bioimpedance sensors, a plurality of pressure sensors, a plurality of light sensors, a plurality of temperature sensors, a plurality of pH sensors, a plurality of perspiration sensors, a plurality of ultrasonic sensors, a plurality of bone growth stimulator sensors, and a plurality of a combination of these sensors. In an aspect, detachable element 100 comprises a body 102 and a plurality of light sensors. In an aspect, detachable element 100 further comprises one or more light emitting sources comprising dual emitters configured for emitting 660 nm and 880 nm light. In an aspect, reusable component 150 comprises an alignment guide 158, the function of which is described in greater detail with reference to FIG. 5. In this example, detachable element 100 is mated to a reusable component by a linear movement, as indicated by the dashed line. In an aspect, the mating motion comprises a rotation perpendicular to the dashed line or twists about the dashed line. In an aspect, detachable element 100 comprises an insulating cover layer on top of its electrodes, forming a barrier between the electrodes and the patient's skin while measurements are being taken.

Figure 12:
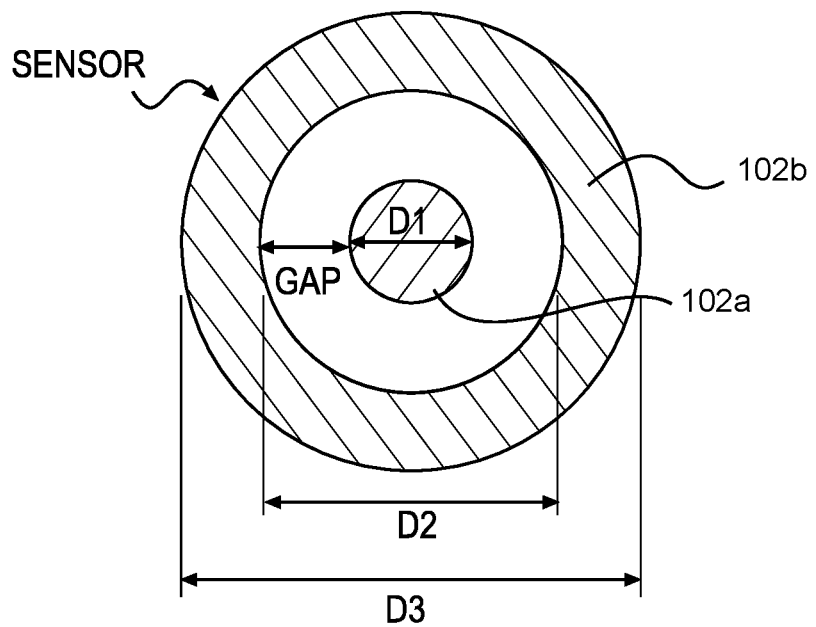
FIG. 12 depicts dimensions of an example sensor in accordance with the present disclosure.
Figure 12:
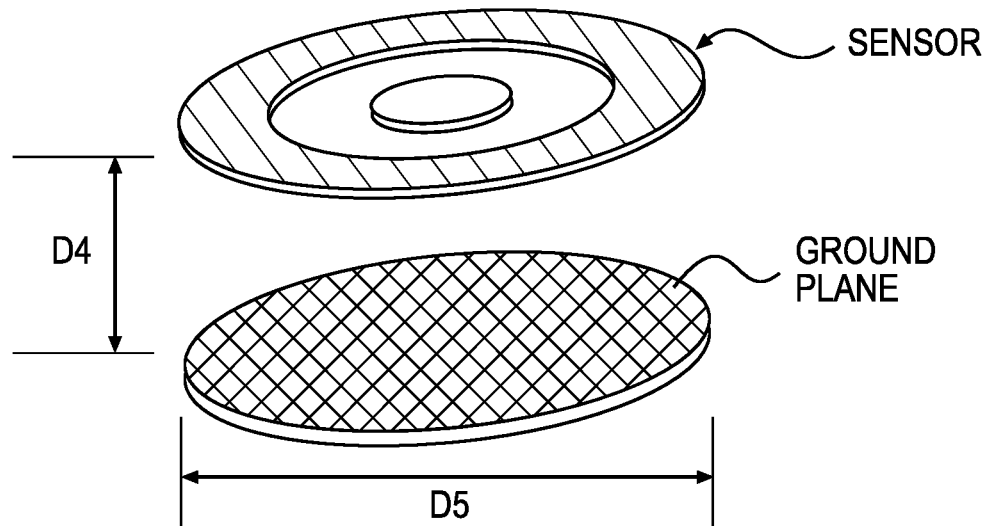

In an aspect, a sensor formed from an annular ring disposed around an inner circular electrode as depicted in FIG. 12. In an aspect, an inner circular electrode is defined by a diameter D1. In an aspect, D1 is about 4.318 mm (0.17 inches). In an aspect, the annular ring is defined by an inner diameter D2 and an outer diameter D3. In an aspect, D2 is about 10.16 mm (0.4 inches). In an aspect, D3 is about 12.7 mm (0.5 inches). In an aspect, D3 is greater than 12.7 mm (0.5 inches), such as about 20.32 mm (0.8 inches). In an aspect, the gap between an inner circular electrode and an outer annular ring is about 2.921 mm (0.115 inches). In an aspect, the gap between an inner circular electrode and an outer annular ring is defined by the formula (D2−D1)/2.

In an aspect, a ground plane is provided. In an aspect, a sensor is separated from a ground plane by a distance D4. In an aspect, D4 is about 0.4064 mm (0.016 inches). In an aspect, a ground plane has a diameter D5. In an aspect, D5 is equal to D3. In an aspect, D5 is greater than D3. In an aspect, D5 is about 28.575 mm (1.125 inches).

In an aspect, the diameter of center electrode 102a is 2.54 mm (0.1 inches). In an aspect, the diameter of center electrode 102a is 2.794 mm (0.11 inches). In an aspect, the diameter of center electrode 102a is 3.048 mm (0.12 inches). In an aspect, the diameter of center electrode 102a is 3.302 mm (0.13 inches). In an aspect, the diameter of center electrode 102a is 3.556 mm (0.14 inches). In an aspect, the diameter of center electrode 102a is 3.81 mm (0.15 inches). In an aspect, the diameter of center electrode 102a is 4.064 mm (0.16 inches). In an aspect, the diameter of center electrode 102a is 4.318 mm (0.17 inches). In an aspect, the diameter of center electrode 102a is 4.572 mm (0.18 inches). In an aspect, the diameter of center electrode 102a is 4.826 mm (0.19 inches). In an aspect, the diameter of center electrode 102a is 5.08 mm (0.2 inches). In an aspect, the diameter of center electrode 102a is 5.588 mm (0.22 inches). In an aspect, the diameter of center electrode 102a is 6.096 mm (0.24 inches). In an aspect, the diameter of center electrode 102a is 6.604 mm (0.26 inches). In an aspect, the diameter of center electrode 102a is 7.112 mm (0.28 inches). In an aspect, the diameter of center electrode 102a is 7.62 mm (0.3 inches). In an aspect, the diameter of center electrode 102a is 8.89 mm (0.35 inches). In an aspect, the diameter of center electrode 102a is 10.16 mm (0.4 inches). In an aspect, the diameter of center electrode 102a is 11.43 mm (0.45 inches). In an aspect, the diameter of center electrode 102a is 12.7 mm (0.5 inches).

In an aspect, the diameter of center electrode 102a is at least 2.54 mm (0.1 inches). In an aspect, the diameter of center electrode 102a is at least 2.794 mm (0.11 inches). In an aspect, the diameter of center electrode 102a is at least 3.048 mm (0.12 inches). In an aspect, the diameter of center electrode 102a is at least 3.302 mm (0.13 inches). In an aspect, the diameter of center electrode 102a is at least 3.556 mm (0.14 inches). In an aspect, the diameter of center electrode 102a is at least 3.81 mm (0.15 inches). In an aspect, the diameter of center electrode 102a is at least 4.064 mm (0.16 inches). In an aspect, the diameter of center electrode 102a is at least 4.318 mm (0.17 inches). In an aspect, the diameter of center electrode 102a is at least 4.572 mm (0.18 inches). In an aspect, the diameter of center electrode 102a is at least 4.826 mm (0.19 inches). In an aspect, the diameter of center electrode 102a is at least 5.08 mm (0.2 inches). In an aspect, the diameter of center electrode 102a is at least 5.588 mm (0.22 inches). In an aspect, the diameter of center electrode 102a is at least 6.096 mm (0.24 inches). In an aspect, the diameter of center electrode 102a is at least 6.604 mm (0.26 inches). In an aspect, the diameter of center electrode 102a is at least 7.112 mm (0.28 inches). In an aspect, the diameter of center electrode 102a is at least 7.62 mm (0.3 inches). In an aspect, the diameter of center electrode 102a is at least 8.89 mm (0.35 inches). In an aspect, the diameter of center electrode 102a is at least 10.16 mm (0.4 inches). In an aspect, the diameter of center electrode 102a is at least 11.43 mm (0.45 inches). In an aspect, the diameter of center electrode 102a is at least 12.7 mm (0.5 inches).

In an aspect, the diameter of center electrode 102a is between 2.54 mm and 3.81 mm (between 0.1 inches and 0.15 inches). In an aspect, the diameter of center electrode 102a is between 3.81 mm and 5.08 mm (between 0.15 inches and 0.2 inches). In an aspect, the diameter of center electrode 102a is between 5.08 mm and 6.35 mm (between 0.2 inches and 0.25 inches). In an aspect, the diameter of center electrode 102a is between 6.35 mm and 7.62 mm (between 0.25 inches and 0.3 inches). In an aspect, the diameter of center electrode 102a is between 7.62 mm and 8.89 mm (between 0.3 inches and 0.35 inches). In an aspect, the diameter of center electrode 102a is between 8.89 mm and 10.16 mm (between 0.35 inches and 0.4 inches). In an aspect, the diameter of center electrode 102a is between 2.54 mm and 5.08 mm (between 0.1 inches and 0.2 inches). In an aspect, the diameter of center electrode 102a is between 2.54 mm and 7.62 mm (between 0.1 inches and 0.3 inches). In an aspect, the diameter of center electrode 102a is between 2.54 mm and 10.16 mm (between 0.1 inches and 0.4 inches). In an aspect, the diameter of center electrode 102a is between 2.54 mm and 12.7 mm (between 0.1 inches and 0.5 inches). In an aspect, the diameter of center electrode 102a is between 5.08 mm and 7.62 mm (between 0.2 inches and 0.3 inches). In an aspect, the diameter of center electrode 102a is between 7.62 mm and 10.16 mm (between 0.3 inches and 0.4 inches). In an aspect, the diameter of center electrode 102a is between 10.16 mm and 12.7 mm (between 0.4 inches and 0.5 inches). In an aspect, the diameter of center electrode 102a is between 2.54 mm and 7.62 mm (between 0.1 inches and 0.3 inches). In an aspect, the diameter of center electrode 102a is between 5.08 mm and 10.16 mm (between 0.2 inches and 0.4 inches). In an aspect, the diameter of center electrode 102a is between 7.62 mm and 12.7 mm (between 0.3 inches and 0.5 inches). In an aspect, the diameter of center electrode 102a is between 2.54 mm and 12.7 mm (between 0.1 inches and 0.5 inches).

In an aspect, an annular or toroidal electrode has an inner diameter and an outer diameter. In an aspect, the inner diameter of toroidal electrode 102b is 2.54 mm (0.1 inches). In an aspect, the inner diameter of toroidal electrode 102b is 5.08 mm (0.2 inches). In an aspect, the inner diameter of toroidal electrode 102b is 7.62 mm (0.3 inches). In an aspect, the inner diameter of toroidal electrode 102b is 10.16 mm (0.4 inches). In an aspect, the inner diameter of toroidal electrode 102b is 12.7 mm (0.5 inches). In an aspect, the inner diameter of toroidal electrode 102b is 15.26 mm (0.6 inches). In an aspect, the inner diameter of toroidal electrode 102b is 17.78 mm (0.7 inches). In an aspect, the inner diameter of toroidal electrode 102b is 20.32 mm (0.8 inches). In an aspect, the inner diameter of toroidal electrode 102b is 22.86 mm (0.9 inches). In an aspect, the inner diameter of toroidal electrode 102b is 25.4 mm (1.0 inches). In an aspect, the inner diameter of toroidal electrode 102b is 30.48 mm (1.2 inches). In an aspect, the inner diameter of toroidal electrode 102b is 35.56 mm (1.4 inches). In an aspect, the inner diameter of toroidal electrode 102b is 40.64 mm (1.6 inches). In an aspect, the inner diameter of toroidal electrode 102b is 45.72 mm (1.8 inches). In an aspect, the inner diameter of toroidal electrode 102b is 50.8 mm (2.0 inches). In an aspect, the inner diameter of toroidal electrode 102b is 63.5 mm (2.5 inches). In an aspect, the inner diameter of toroidal electrode 102b is 76.2 mm (3.0 inches).

In an aspect, the inner diameter of toroidal electrode 102b is at least 2.54 mm (0.1 inches). In an aspect, the inner diameter of toroidal electrode 102b is at least 5.08 mm (0.2 inches). In an aspect, the inner diameter of toroidal electrode 102b is at least 7.62 mm (0.3 inches). In an aspect, the inner diameter of toroidal electrode 102b is at least 10.16 mm (0.4 inches). In an aspect, the inner diameter of toroidal electrode 102b is at least 12.7 mm (0.5 inches). In an aspect, the inner diameter of toroidal electrode 102b is at least 15.26 mm (0.6 inches). In an aspect, the inner diameter of toroidal electrode 102b is at least 17.78 mm (0.7 inches). In an aspect, the inner diameter of toroidal electrode 102b is at least 20.32 mm (0.8 inches). In an aspect, the inner diameter of toroidal electrode 102b is at least 22.86 mm (0.9 inches). In an aspect, the inner diameter of toroidal electrode 102b is at least 25.4 mm (1.0 inch). In an aspect, the inner diameter of toroidal electrode 102b is at least 30.48 mm (1.2 inches). In an aspect, the inner diameter of toroidal electrode 102b is at least 35.56 mm (1.4 inches). In an aspect, the inner diameter of toroidal electrode 102b is at least 40.64 mm (1.6 inches). In an aspect, the inner diameter of toroidal electrode 102b is at least 45.72 mm (1.8 inches). In an aspect, the inner diameter of toroidal electrode 102b is at least 50.8 mm (2.0 inches). In an aspect, the inner diameter of toroidal electrode 102b is at least 63.5 mm (2.5 inches). In an aspect, the inner diameter of toroidal electrode 102b is at least 76.2 mm (3.0 inches).

In an aspect, the inner diameter of toroidal electrode 102b is between 2.54 mm and 12.7 mm (between 0.1 inches and 0.5 inches). In an aspect, the inner diameter of toroidal electrode 102b is between 2.54 mm and 25.4 mm (between 0.1 inches and 1 inch). In an aspect, the inner diameter of toroidal electrode 102b is between 2.54 mm and 50.8 mm (between 0.1 inches and 2.0 inches). In an aspect, the inner diameter of toroidal electrode 102b is between 2.54 mm and 76.2 mm (between 0.1 inches and 3.0 inches). In an aspect, the inner diameter of toroidal electrode 102b is between 12.7 mm and 25.4 mm (between 0.5 inches and 1.0 inch). In an aspect, the inner diameter of toroidal electrode 102b is between 12.7 mm and 38.1 mm (between 0.5 inches and 1.5 inches). In an aspect, the inner diameter of toroidal electrode 102b is between 25.4 mm and 38.1 mm (between 1.0 inch and 1.5 inches). In an aspect, the inner diameter of toroidal electrode 102b is between 38.1 mm and 50.8 mm (between 1.5 inches and 2.0 inches). In an aspect, the inner diameter of toroidal electrode 102b is between 50.8 mm and 76.2 mm (between 2.0 inches and 3.0 inches).

In an aspect, the outer diameter of toroidal electrode 102b is 2.54 mm (0.1 inches). In an aspect, the outer diameter of toroidal electrode 102b is 5.08 mm (0.2 inches). In an aspect, the outer diameter of toroidal electrode 102b is 7.62 mm (0.3 inches). In an aspect, the outer diameter of toroidal electrode 102b is 10.16 mm (0.4 inches). In an aspect, the outer diameter of toroidal electrode 102b is 12.7 mm (0.5 inches). In an aspect, the outer diameter of toroidal electrode 102b is 15.26 mm (0.6 inches). In an aspect, the outer diameter of toroidal electrode 102b is 17.78 mm (0.7 inches). In an aspect, the outer diameter of toroidal electrode 102b is 20.32 mm (0.8 inches). In an aspect, the outer diameter of toroidal electrode 102b is 22.86 mm (0.9 inches). In an aspect, the outer diameter of toroidal electrode 102b is 25.4 mm (1.0 inches). In an aspect, the outer diameter of toroidal electrode 102*b* is 30.48 mm (1.2 inches). In an aspect, the outer diameter of toroidal electrode 102*b* is 35.56 mm (1.4 inches). In an aspect, the outer diameter of toroidal electrode 102*b* is 40.64 mm (1.6 inches). In an aspect, the outer diameter of toroidal electrode 102*b* is 45.72 mm (1.8 inches). In an aspect, the outer diameter of toroidal electrode 102*b* is 50.8 mm (2.0 inches). In an aspect, the outer diameter of toroidal electrode 102*b* is 63.5 mm (2.5 inches). In an aspect, the outer diameter of toroidal electrode 102*b* is 76.2 mm (3.0 inches).

In an aspect, the outer diameter of toroidal electrode 102*b* is at least 2.54 mm (0.1 inches). In an aspect, the outer diameter of toroidal electrode 102*b* is at least 5.08 mm (0.2 inches). In an aspect, the outer diameter of toroidal electrode 102*b* is at least 7.62 mm (0.3 inches). In an aspect, the outer diameter of toroidal electrode 102*b* is at least 10.16 mm (0.4 inches). In an aspect, the outer diameter of toroidal electrode 102*b* is at least 12.7 mm (0.5 inches). In an aspect, the outer diameter of toroidal electrode 102*b* is at least 15.26 mm (0.6 inches). In an aspect, the outer diameter of toroidal electrode 102*b* is at least 17.78 mm (0.7 inches). In an aspect, the outer diameter of toroidal electrode 102*b* is at least 20.32 mm (0.8 inches). In an aspect, the outer diameter of toroidal electrode 102*b* is at least 22.86 mm (0.9 inches). In an aspect, the outer diameter of toroidal electrode 102*b* is at least 25.4 mm (1.0 inch). In an aspect, the outer diameter of toroidal electrode 102*b* is at least 30.48 mm (1.2 inches). In an aspect, the outer diameter of toroidal electrode 102*b* is at least 35.56 mm (1.4 inches). In an aspect, the outer diameter of toroidal electrode 102*b* is at least 40.64 mm (1.6 inches). In an aspect, the outer diameter of toroidal electrode 102*b* is at least 45.72 mm (1.8 inches). In an aspect, the outer diameter of toroidal electrode 102*b* is at least 50.8 mm (2.0 inches). In an aspect, the outer diameter of toroidal electrode 102*b* is at least 63.5 mm (2.5 inches). In an aspect, the outer diameter of toroidal electrode 102*b* is at least 76.2 mm (3.0 inches).

In an aspect, the outer diameter of toroidal electrode 102*b* is between 2.54 mm and 12.7 mm (between 0.1 inches and 0.5 inches). In an aspect, the outer diameter of toroidal electrode 102*b* is between 2.54 mm and 25.4 mm (between 0.1 inches and 1 inch). In an aspect, the outer diameter of toroidal electrode 102*b* is between 2.54 mm and 50.8 mm (between 0.1 inches and 2.0 inches). In an aspect, the outer diameter of toroidal electrode 102*b* is between 2.54 mm and 76.2 mm (between 0.1 inches and 3.0 inches). In an aspect, the outer diameter of toroidal electrode 102*b* is between 12.7 mm and 25.4 mm (between 0.5 inches and 1.0 inch). In an aspect, the outer diameter of toroidal electrode 102*b* is between 12.7 mm and 38.1 mm (between 0.5 inches and 1.5 inches). In an aspect, the outer diameter of toroidal electrode 102*b* is between 25.4 mm and 38.1 mm (between 1.0 inch and 1.5 inches). In an aspect, the outer diameter of toroidal electrode 102*b* is between 38.1 mm and 50.8 mm (between 1.5 inches and 2.0 inches). In an aspect, the outer diameter of toroidal electrode 102*b* is between 50.8 mm and 76.2 mm (between 2.0 inches and 3.0 inches).

In an aspect, D4 is 0.254 mm (0.01 inches). In an aspect, D4 is 0.2794 mm (0.011 inches). In an aspect, D4 is 0.3048 mm (0.012 inches). In an aspect, D4 is 0.3302 mm (0.013 inches). In an aspect, D4 is 0.3556 mm (0.014 inches). In an aspect, D4 is 0.381 mm (0.015 inches). In an aspect, D4 is 0.4064 mm (0.016 inches). In an aspect, D4 is 0.4318 mm (0.017 inches). In an aspect, D4 is 0.4572 mm (0.018 inches). In an aspect, D4 is 0.4826 mm (0.019 inches). In an aspect, D4 is 0.508 mm (0.02 inches). In an aspect, D4 is 0.635 mm (0.025 inches). In an aspect, D4 is 0.762 mm (0.03 inches).

In an aspect, D4 is at least 0.254 mm (0.01 inches). In an aspect, D4 is at least 0.2794 mm (0.011 inches). In an aspect, D4 is at least 0.3048 mm (0.012 inches). In an aspect, D4 is at least 0.3302 mm (0.013 inches). In an aspect, D4 is at least 0.3556 mm (0.014 inches). In an aspect, D4 is at least 0.381 mm (0.015 inches). In an aspect, D4 is at least 0.4064 mm (0.016 inches). In an aspect, D4 is at least 0.4318 mm (0.017 inches). In an aspect, D4 is at least 0.4572 mm (0.018 inches). In an aspect, D4 is at least 0.4826 mm (0.019 inches). In an aspect, D4 is at least 0.508 mm (0.02 inches). In an aspect, D4 is at least 0.635 mm (0.025 inches). In an aspect, D4 is at least 0.762 mm (0.03 inches).

In an aspect, D4 is between 0.254 mm and 0.508 mm (between 0.01 inches and 0.02 inches). In an aspect, D4 is between 0.254 mm and 0.762 mm (between 0.01 inches and 0.03 inches). In an aspect, D4 is between 0.381 mm and 0.508 mm (between 0.015 inches and 0.02 inches). In an aspect, D4 is between 0.381 mm and 0.762 mm (between 0.015 inches and 0.03 inches). In an aspect, D4 is between 0.508 mm and 0.762 mm (between 0.02 inches and 0.03 inches).

In an aspect, D5 is between 2.54 mm and 12.7 mm (between 0.1 inches and 0.5 inches). In an aspect, D5 is between 2.54 mm and 25.4 mm (between 0.1 inches and 1 inch). In an aspect, D5 is between 2.54 mm and 50.8 mm (between 0.1 inches and 2.0 inches). In an aspect, D5 is between 2.54 mm and 76.2 mm (between 0.1 inches and 3.0 inches). In an aspect, D5 is between 12.7 mm and 25.4 mm (between 0.5 inches and 1.0 inch). In an aspect, D5 is between 12.7 mm and 38.1 mm (between 0.5 inches and 1.5 inches). In an aspect, D5 is between 25.4 mm and 38.1 mm (between 1.0 inch and 1.5 inches). In an aspect, D5 is between 38.1 mm and 50.8 mm (between 1.5 inches and 2.0 inches). In an aspect, D5 is between 50.8 mm and 76.2 mm (between 2.0 inches and 3.0 inches).

Figure 2:
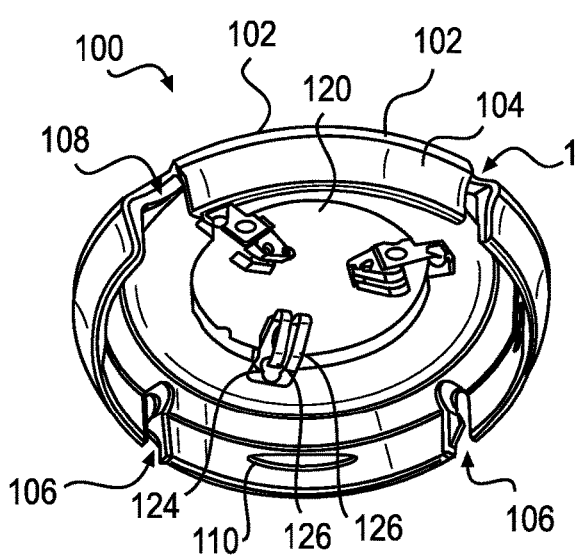
FIG. 2 is a perspective view of the underside of the detachable element of FIG. 1B, in accordance with the present disclosure.

FIG. 2 is a perspective view of the underside of detachable element 100 of FIG. 1B, in accordance with the present disclosure. In an aspect, detachable element 100 comprises a body 102 having, in this example, four wings 104 separated by gaps 106 and alignment feature 108. In an aspect, body 102 comprises up to twenty wings, such as up to five wings, up to six wings, up to seven wings, up to eight wings, up to nine wings, up to ten wings, up to eleven wings, up to twelve wings, up to thirteen wings, up to fourteen wings, up to fifteen wings, up to sixteen wings, up to seventeen wings, up to eighteen wings, or up to nineteen wings. In an aspect, alignment feature 108 is configured to mate with the alignment guide 158 of reusable component 150 (e.g. shown in FIG. 3). In an aspect, gaps 106 cannot mate with alignment guide 158, for example, because gaps 106 are narrower than alignment feature 108.

In an aspect, contactors 124 are attached to a printed circuit board (PCB) 120 that is coupled to the body 102. In one aspect, a plurality of contactors are coupled to body 102, such as up to one hundred contactors, up to ninety contactors, up to eighty contactors, up to seventy contactors, up to sixty contactors, up to fifty contactors, up to forty contactors, up to thirty contactors, up to twenty contactors, up to fifteen contactors, up to ten contactors, up to nine contactors, up to eight contactors, up to seven contactors, up to six contactors, up to five contactors, up to four contactors, or up to three contactors. In this example, each contactor 124 has two cantilever elements 126 that are independently movable. In an aspect, each contactor 124 comprises up to ten cantilever elements, such as up to nine cantilever elements, up to eight cantilever elements, up to seven cantilever elements, up to six cantilever elements, up to five cantilever elements, up to four cantilever elements, or up to three cantilever elements. In an aspect, the inside surface of at least some of wings 104 have a retention feature 110 that, in this example, extends out from the inside surface of the wing 104. In an aspect, each of wings 104 has a retention feature 110. In an aspect, retention feature 110 is a recess. In an aspect, each contactor 124 provides an electrical connection between an electrode of body 102 and PCB 120.

Figure 3:
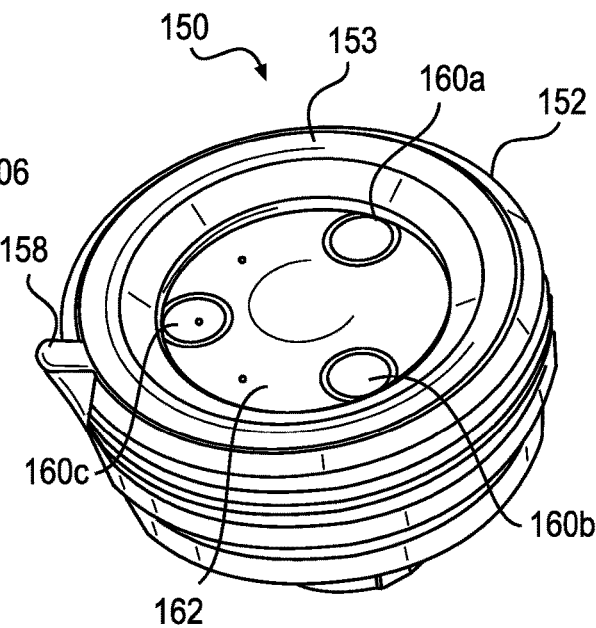
FIG. 3 is a perspective view of the top surface of the reusable component, in accordance with the present disclosure.

FIG. 3 is a perspective view of the top surface of reusable component 150, in accordance with the present disclosure. In an aspect, the reusable component 150 comprises a body 152 to which is coupled to a PCB having a top surface 162. In an aspect, a plurality of planar contact surfaces are coupled to surface 162, such as up to 100 planar contact surfaces, up to 90 planar contact surfaces, up to 80 planar contact surfaces, up to 70 planar contact surfaces, up to 60 planar contact surfaces, up to 50 planar contact surfaces, up to 40 planar contact surfaces, up to 30 planar contact surfaces, up to 20 planar contact surfaces, up to 10 planar contact surfaces, up to 9 planar contact surfaces, up to 8 planar contact surfaces, up to 7 planar contact surfaces, up to 6 planar contact surfaces, up to 5 planar contact surfaces, up to 4 planar contact surfaces, or up to 3 planar contact surfaces.

In an aspect, three planar contact surfaces 160*a*, 160*b*, and 160*c* are coupled to surface 162. In an aspect, contact surfaces 160*a*, 160*b*, 160*c* are formed as copper layers on the surface 162 and are generally coplanar (within a few thousands of an inch) with the surface 162. Contact surfaces 160*a*, 160*b*, 160*c* are conductive and, in an aspect, connected to circuits that are electrically isolated from each other. In an aspect, contact surfaces 160*a*, 160*b*, 160*c* comprise a surface coating of a noble metal, for example, gold, that may be mixed with other materials to improve physical properties, for example, abrasion resistance.

In an aspect, contact surfaces 160*a*, 160*b*, 160*c* are each planar and lie on a common plane that is parallel to the retention groove.

In an aspect, a contactor 124 comprises conductive material. In an aspect, a contactor 124 comprises a conductive compressible foam. In an aspect, a contactor 124 is conductively attached to PCB 120 and is configured to compress against any one of three planar contact surfaces 160*a*, 160*b*, and 160*c* when detachable element 100 (e.g. shown in FIG. 2) is installed on reusable component 150. In an aspect, a contactor 124 is configured to compress against any one of three planar contact surfaces 160*a*, 160*b*, and 160*c* when detachable element 100 (e.g. shown in FIG. 2) is installed on reusable component 150.

In an aspect, a contactor 124 comprises a non-conductive material. In an aspect, a contactor 124 comprises a non-conductive compressible foam. In an aspect, a contactor 124 comprises a non-conductive spring element and a separate conductive element, where the conductive element is conductively attached to PCB 120 on one end and to a free end of the non-conductive spring element. In an aspect, a conductive element exposed on a free end of a non-conductive spring element is held against any one of three planar contact surfaces 160*a*, 160*b*, and 160*c* by the non-conductive spring element when detachable element 100 (e.g. shown in FIG. 2) is installed on reusable component 150. In an aspect, a conductive element is a conductive wire.

In an aspect, a cantilever element 126 comprises a conductive material. In an aspect, a cantilever element 126 comprises a conductive compressible foam. In an aspect, a cantilever element 126 comprise a metallic coil spring.

In an aspect, a cantilever element 126 comprises a non-conductive material. In an aspect, a cantilever element 126 comprises a non-conductive compressible foam.

In an aspect, a contactor 124 comprises a compressible pogo pin, where the pogo pin is of suitable height in its compressed state to conductively join PCB 120 to planar contact surfaces 160*a*, 160*b*, and 160*c* when detachable element 100 (e.g. shown in FIG. 2) is installed on reusable component 150.

Figure 4:
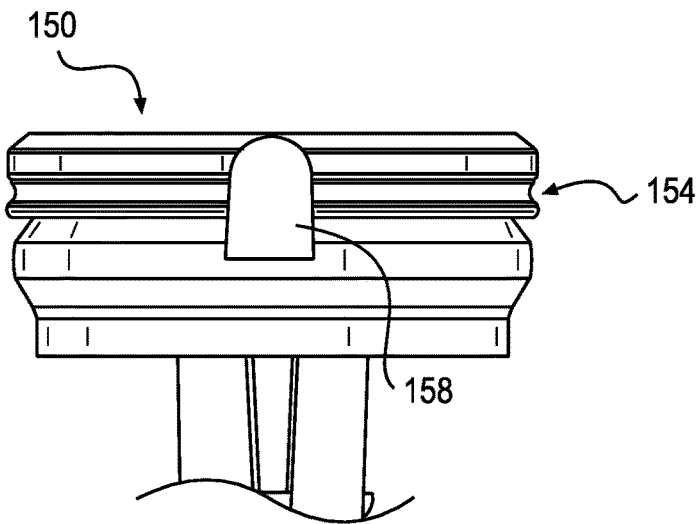
FIG. 4 is a side view of the reusable component, in accordance with the present disclosure.

FIG. 4 is a side view of the reusable component 150, in accordance with the present disclosure. In an aspect, reusable component 150 comprises a retention groove 154 and alignment guide 158. In an aspect, the retention groove 154 extends around only a portion of a circumference of reusable component 150. Likewise, in an aspect, retention feature 110 (e.g. shown in FIG. 2) extends around only a portion of a circumference of detachable element 100 (e.g. shown in FIG. 2). In an aspect, retention groove 154 is partially configured as a flush or protruding element. In an aspect, retention groove 154 may have any geometry selected to interact with one or more of retention feature 110 (e.g. shown in FIG. 2), each having a complementary geometry, so as to retain detachable element 100 (e.g. shown in FIG. 2) on the reusable component 150 under determined loads.

Figure 5:
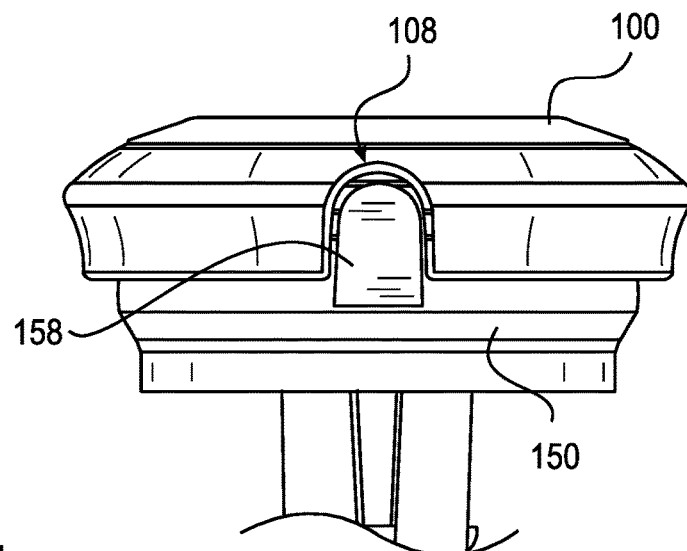
FIG. 5 is a side view of the detachable element mated with the reusable component, in accordance with the present disclosure.

FIG. 5 is a side view of detachable element 100 mated with reusable component 150, in accordance with the present disclosure. In an aspect, alignment feature 108 is mated with alignment guide 158.

Figure 6:
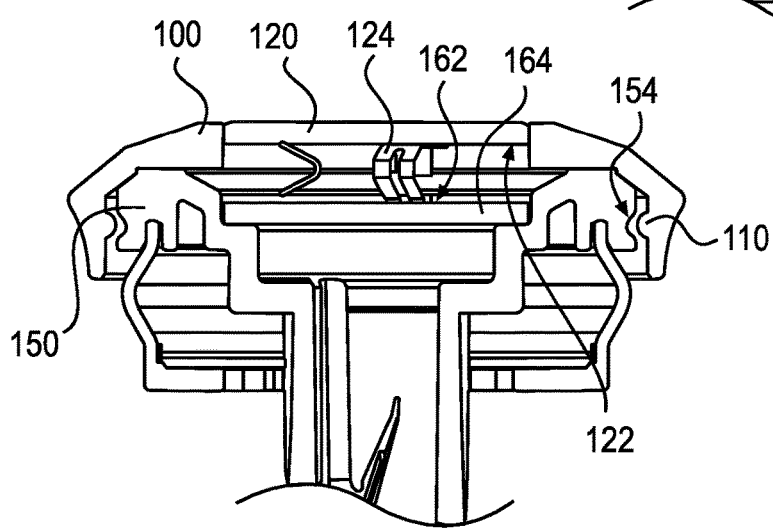
FIG. 6 is a cross-section of the side view of FIG. 5, in accordance with the present disclosure.

FIG. 6 is a cross-section of the side view of FIG. 5, in accordance with the present disclosure. Retention feature 110 is engaged with retention groove 154. In an aspect, contactor 124 is coupled to the underside surface 122 of the PCB 120. In an aspect, free length of contactor 124 is greater than the separation distance between underside surface 122 and top surface 162 of PCB 164.

Figure 7A:
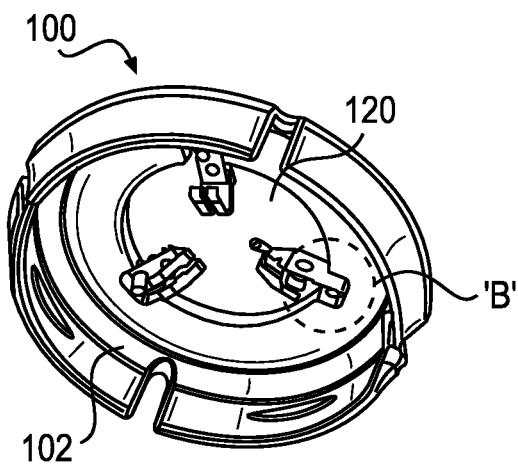
FIG. 7A is another perspective view of the underside of the detachable element of FIG. 1B, in accordance with the present disclosure.
Figure 8:
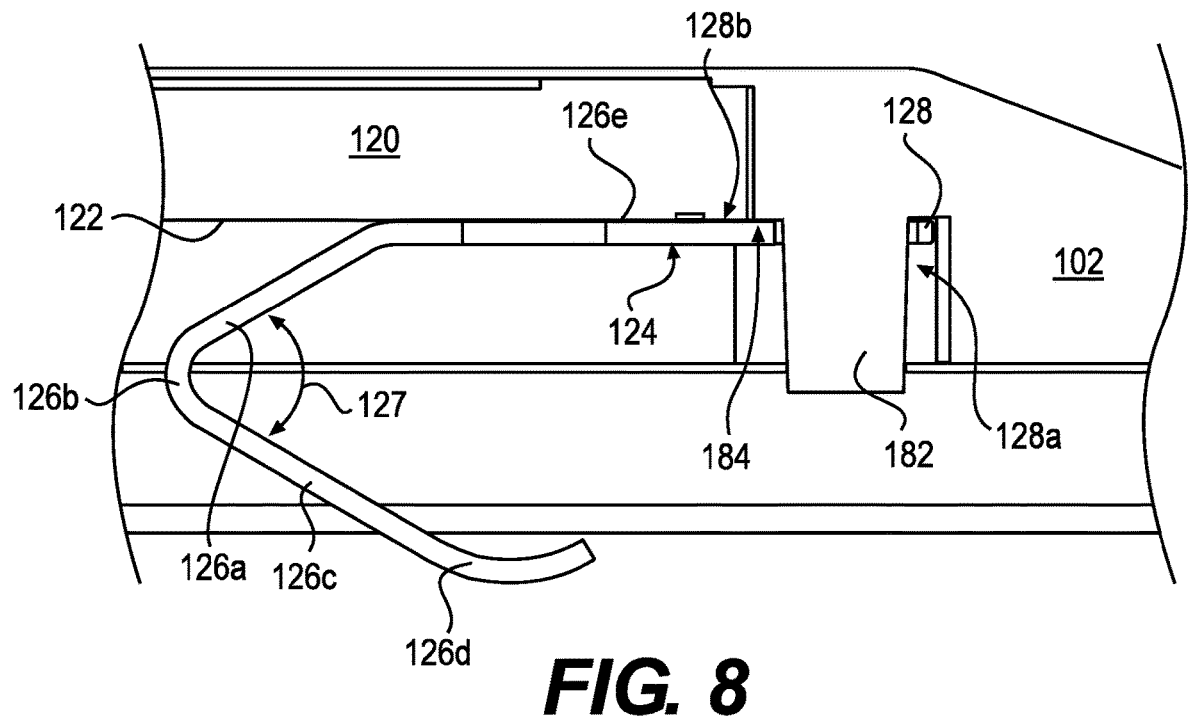
FIG. 8 is an enlarged cross-section of the region marked "B" in FIG. 7A, in accordance with the present disclosure.

FIG. 7A is another perspective view of the underside of the detachable element 100 of FIG. 1B, in accordance with the present disclosure. An enlarged view of region 'B' is shown in FIG. 8.

Figure 7B:
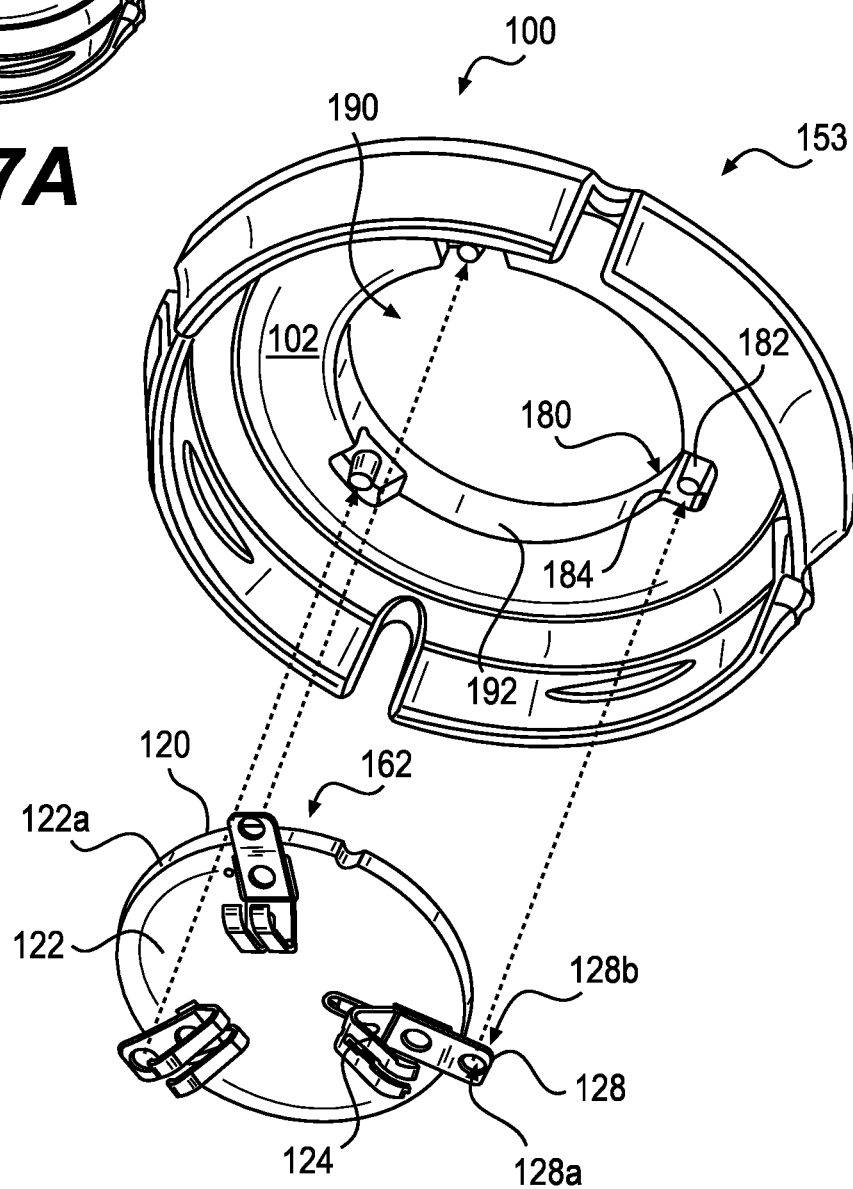
FIG. 7B is a partially exploded view of the detachable element of FIG. 7A, in accordance with the present disclosure.

FIG. 7B is a partially exploded view of the detachable element 100 of FIG. 7A, in accordance with the present disclosure. In an aspect, body 102 has a center hole 190 with several retention pockets 180 around perimeter 192. In an aspect, each retention pocket 180 has a staking post 182 and a reference surface 184.

In an aspect, PCB 120 has an underside surface 122 with an outer edge 122*a*. In an aspect, outer edge 122*a* is circular. In an aspect, outer edge 122*a* may be of any shape. In an aspect, the contactors 124 have flanges 128 that extend beyond the outer edge 122*a*. In an aspect, each flange 128 has a center hole 128*a* and a top surface 128*b*. In an aspect, when PCB 120 is brought into contact with body 102, center holes 128*a* will fit over posts 182 as indicated by the dashed-line arrows and top surfaces 128*b* will contact reference surfaces 184.

In an aspect, the arrangement of PCB 120 fits closely into hole 190, where flanges 128 extending beyond the edge of outer edge 122*a*, and the reference surfaces adjacent to hole 190 allow PCB 120 to be inserted into hole 190 from below. In an aspect, by selection of an appropriate offset distance from reference surface 184 to top surface 153 (not visible in FIG. 7B, shown in FIG. 3) of body 102, surface 162 (not visible in FIG. 7B, shown in FIG. 3) of PCB 120 can be held coplanar with top surface 153 or at a determined offset above or below top surface 153. In an aspect, the distance from reference surface 184 to top surface 153 may be equal to, greater than, or less than the thickness of PCB 120. In an aspect, one or more of the flanges 128 may be functionally replaced with other elements that are not integral with contactors 124, for example, a formed sheet metal tab, that is coupled to PCB 120 and extends beyond outer edge 122*a*.

FIG. 8 is an enlarged cross-section of the region marked 'B' in FIG. 7A, in accordance with the present disclosure. In an aspect, top surface 128*b* is shown in contact with reference surface 184 and post 182 passing through center hole 128*a*.

In FIG. 8, cantilever element 126 is formed by base segment 126*e* that is coupled, for example, by soldering, to PCB 120, a cantilever element comprising a first linear segment 126*a*, an angled coupler 126*b*, a second linear segment 126*c*, and a curved contact segment 126*d*. In an aspect, when detachable element 100 (e.g. as shown in FIG. 1B) is brought together with reusable component 150, as indicated in FIG. 1B, curved contact segment 126*d* will contact planar contact surface 160*a* (e.g. as shown in FIG. 3). In an aspect, as the free height of contactor 124 is greater than the final gap between surfaces 122 and 166, as seen in FIG. 6, contactor 124 must compress as detachable element 100 (e.g. as shown in FIG. 1B) is seated onto reusable component 150 (e.g. as shown in FIG. 1B). In an aspect, as this compression occurs, first linear segment 126*a*, angled coupler 126*b*, and second linear segment 126*c* of the cantilever element will elastically deform and the included angle 127 between segments 126*a* and 126*c* will decrease. In an aspect, for example, when first linear segment 126*a* is shorter than second linear segment 126*c*, the point of contact between curved contact segment 126*d* and planar contact surface 160*a* (e.g. as shown in FIG. 3) will move in an arc having both vertical and horizontal movement, in the reference frame of FIG. 8. In an aspect, the horizontal motion creates a desirable sliding contact between curved contact segment 126*d* and planar contact surface 160*a* (e.g. as shown in FIG. 3), which improves the quality and reliability of the electrical contact between contact segment 126*d* and planar contact surface 160*a*.

In an aspect, contactor 124 may be formed as any compliant element that accomplishes the same function of providing an electrical connection between an element of PCB 120 and a conductive element of reusable component 150 (e.g. shown in FIG. 3), for example, a planar contact surface 160*a* (e.g. shown in FIG. 3), when compressed between surfaces 122 and 162 (e.g. shown in FIG. 3). In an aspect, contactor 124 may be any compliant element having a conductive portion, for example, a pogo pin, a coil spring, a conductive foam pad, or a directionally conductive adhesive.

In an aspect, detachable element 100 and reusable component 150 (e.g. shown in FIG. 1B) may be configured such that the act of mating detachable element 100 and reusable component 150 (e.g. shown in FIG. 1B) induces a twisting or sliding motion that induces a scrubbing contact of contactor 124 and planar contact surface 160*a* (e.g. shown in FIG. 3).

Figure 9:
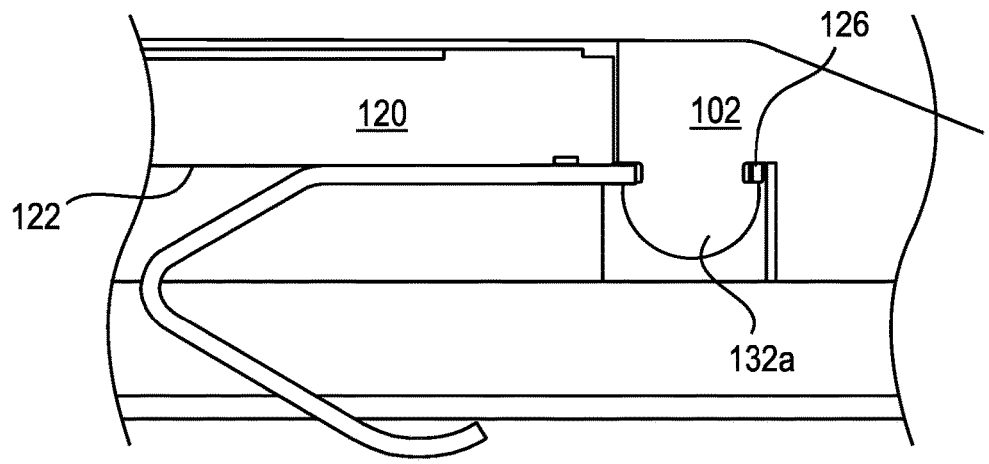
FIG. 9 is a second cross-section showing the configuration of the region "B" after a heat staking operation has been completed, in accordance with the present disclosure.

FIG. 9 is a second cross-section showing the configuration of the region 'B' after a heat-staking operation has been complete, in accordance with the present disclosure. In an aspect, post 182 (e.g. shown in FIG. 7B) has been reshaped, for example, by heat staking, to form a cap 132*a* with an enlarged diameter that overlaps flange 128, thereby retaining underside surface 122 of PCB 120 to body 102. In an aspect, PCB 120 may be retained to body 102 by mechanical attachment, for example, a fastener (not shown in FIG. 9), or by clamping, for example, by insertion of a retention fitting (not shown in FIG. 9), by bonding, for example, UV-cured cyanoacrylate (not shown in FIG. 9), or by any attachment method known to those of skill in the art.

Figure 10:
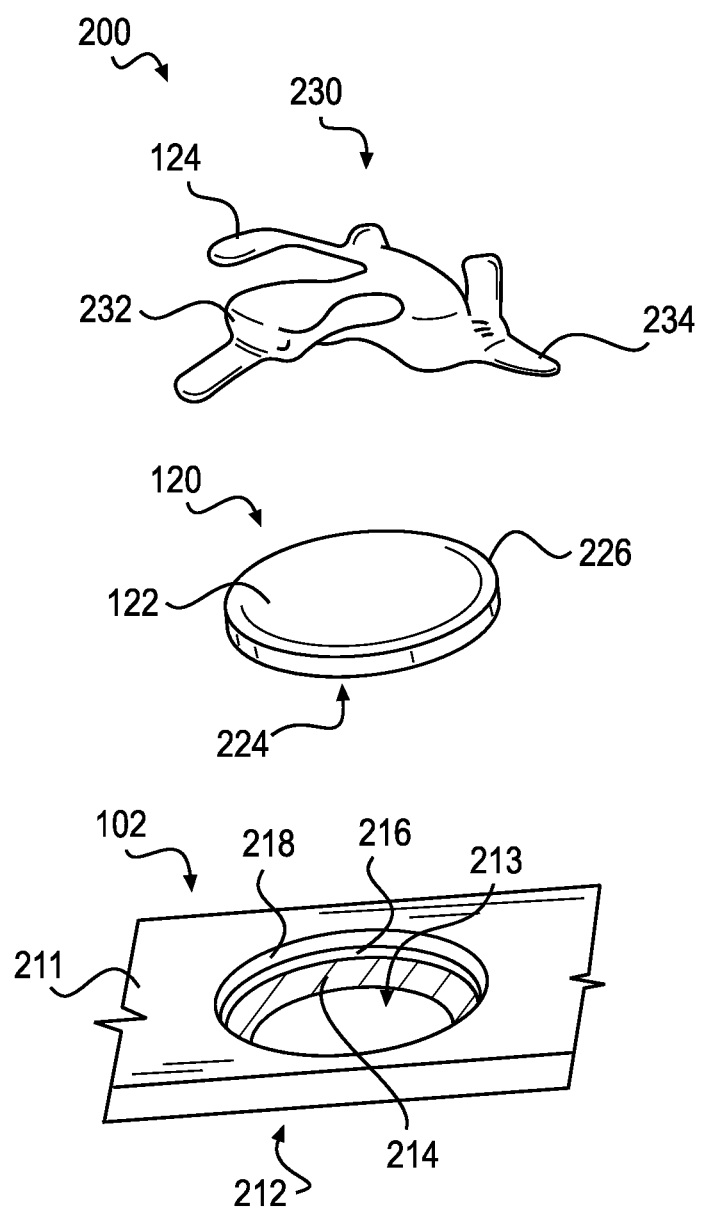
FIG. 10 is an exploded view of an assembly comprising a frame, a PCB, and a retainer.

FIG. 10 is an exploded view of an assembly 200 comprising a body 102, a PCB 120, and a retainer 230. In an aspect, body 102 is a portion of a housing of a device. In an aspect, assembly 200 is a disposable attachment to a device.

Body 102 comprises an opening 213 that, in this example, is a circular through-hole penetrating from a first surface 212 to a second surface 211. In an aspect, opening 213 is a notch or other open shape and may have an arbitrary shape defined by a perimeter 214. In this example, there is a lip or surface 216 recessed from a second surface 211. In this example, surface 216 is separated from a first surface 212 by a distance that is equal to the thickness of PCB 120. In an aspect, the separation of surfaces 212 and 216 is dependent upon the configuration of retainer 230. Surface 216 may have a diameter defined by a perimeter 218. In an aspect, surface 216 is coincident with second surface 211. In one aspect, surface 216 is comprised of multiple separate surfaces (not shown in FIG. 10) adjacent to opening 213, wherein multiple separate surfaces may be coplanar or may be displaced from each other.

In an aspect, PCB 120 has a thickness of 0.127 mm (0.005 inches). In an aspect, PCB 120 has a thickness of 0.254 mm (0.01 inches). In an aspect, PCB 120 has a thickness of 0.3048 mm (0.012 inches). In an aspect, PCB 120 has a thickness of 0.3556 mm (0.014 inches). In an aspect, PCB 120 has a thickness of 0.4064 mm (0.016 inches). In an aspect, PCB 120 has a thickness of 0.4572 mm (0.018 inches). In an aspect, PCB 120 has a thickness of 0.508 mm (0.02 inches). In an aspect, PCB 120 has a thickness of 0.635 mm (0.025 inches). In an aspect, PCB 120 has a thickness of 0.762 mm (0.03 inches). In an aspect, PCB 120 has a thickness of 1.016 mm (0.04 inches). In an aspect, PCB 120 has a thickness of 1.27 mm (0.05 inches).

In an aspect, PCB 120 has a thickness of at least 0.127 mm (0.005 inches). In an aspect, PCB 120 has a thickness of at least 0.254 mm (0.01 inches). In an aspect, PCB 120 has a thickness of at least 0.3048 mm (0.012 inches). In an aspect, PCB 120 has a thickness of at least 0.3556 mm (0.014 inches). In an aspect, PCB 120 has a thickness of at least 0.4064 mm (0.016 inches). In an aspect, PCB 120 has a thickness of at least 0.4572 mm (0.018 inches). In an aspect, PCB 120 has a thickness of at least 0.508 mm (0.02 inches). In an aspect, PCB 120 has a thickness of at least 0.635 mm (0.025 inches). In an aspect, PCB 120 has a thickness of at least 0.762 mm (0.03 inches). In an aspect, PCB 120 has a thickness of at least 1.016 mm (0.04 inches). In an aspect, PCB 120 has a thickness of at least 1.27 mm (0.05 inches).

In an aspect, PCB 120 has a thickness of between 0.127 mm and 0.254 mm (between 0.005 inches and 0.01 inches). In an aspect, PCB 120 has a thickness of between 0.127 mm and 0.381 mm (between 0.005 inches and 0.015 inches). In an aspect, PCB 120 has a thickness of between 0.127 mm and 0.508 mm (between 0.005 inches and 0.02 inches). In an aspect, PCB 120 has a thickness of between 0.127 mm and 0.635 mm (between 0.005 inches and 0.025 inches). In an aspect, PCB 120 has a thickness of between 0.127 mm and 0.762 mm (between 0.005 inches and 0.03 inches). In an aspect, PCB 120 has a thickness of between 0.127 mm and 1.016 mm (between 0.005 inches and 0.04 inches). In an aspect, PCB 120 has a thickness of between 0.127 mm and 1.27 mm (between 0.005 inches and 0.05 inches). In an aspect, PCB 120 has a thickness of between 0.254 mm and 0.381 mm (between 0.01 inches and 0.015 inches). In an aspect, PCB 120 has a thickness of between 0.254 mm and 0.508 mm (between 0.01 inches and 0.02 inches). In an aspect, PCB 120 has a thickness of between 0.254 mm and 0.635 mm (between 0.01 inches and 0.025 inches). In an aspect, PCB 120 has a thickness of between 0.254 mm and 0.762 mm (between 0.01 inches and 0.03 inches). In an aspect, PCB 120 has a thickness of between 0.254 mm and 1.016 mm (between 0.01 inches and 0.04 inches). In an aspect, PCB 120 has a thickness of between 0.254 mm and 1.27 mm (between 0.01 inches and 0.05 inches). In an aspect, PCB 120 has a thickness of between 0.381 mm and 0.508 mm (between 0.015 inches and 0.02 inches). In an aspect, PCB 120 has a thickness of between 0.381 mm and 0.635 mm (between 0.015 inches and 0.025 inches). In an aspect, PCB 120 has a thickness of between 0.381 mm and 1.27 mm (between 0.015 inches and 0.05 inches). In an aspect, PCB 120 has a thickness of between 0.508 mm and 0.762 mm (between 0.02 inches and 0.03 inches). In an aspect, PCB 120 has a thickness of between 0.508 mm and 1.27 mm (between 0.02 inches and 0.05 inches). In an aspect, PCB 120 has a thickness of between 0.762 mm and 1.016 mm (between 0.03 inches and 0.04 inches). In an aspect, PCB 120 has a thickness of between 0.762 mm and 1.27 mm (between 0.03 inches and 0.05 inches). In an aspect, PCB 120 has a thickness of between 1.016 mm and 1.27 mm (between 0.04 inches and 0.05 inches).

PCB 120 is, in this example, a flat substrate of a nonconductive material, for example FR4, that is typical of printed circuit board fabrication processes. In an aspect, PCB 120 is a sensor. In one aspect, a sensor is selected from the group consisting of a bioimpedance sensor, a photodetector, a temperature sensor, a pH sensor, a perspiration sensor, an ultrasonic sensor, a bone growth stimulator sensor, and a combination thereof. PCB 120 has an underside surface 122 and an upper surface 224 that is parallel to the underside surface 122 and separated from the underside surface 122 by a thickness. PCB 120 has a perimeter 226 that, in this example, is circular and matches surface 216 of body 102. In an aspect, the shape of perimeter 226 is arbitrary. In an aspect, the shape of perimeter 226 is oval-shaped. In an aspect, the shape of perimeter 226 is square-shaped.

Retainer 230 comprises a body 232 and a plurality of tabs 234 formed such that a portion of retainer 230 extends beyond the perimeter of PCB 120 when retainer 230 is attached to PCB 120. Tabs 234 are positioned and shaped to contact surface 216 when the joined PCB-retainer subassembly is inserted into opening 213.

In an aspect, retainer 230 is strictly a mechanical positioning element that may be soldered to PCB 120 or attached via any other method, including adhesives and mechanical attachment such as a rivet or screw. In an aspect, a portion of retainer 230 is a conductive circuit element, such as a spring contactor 124 intended to make conductive contact with an external circuit element (not shown in FIG. 10) associated with body 102. In an aspect, retainer 230 is an assembly comprising one or more conductive elements and one or more non-conductive elements. In an aspect, retainer 230 is formed from metal. In one aspect, retainer 230 is formed from a non-metal material such as a plastic.

Figure 11A:
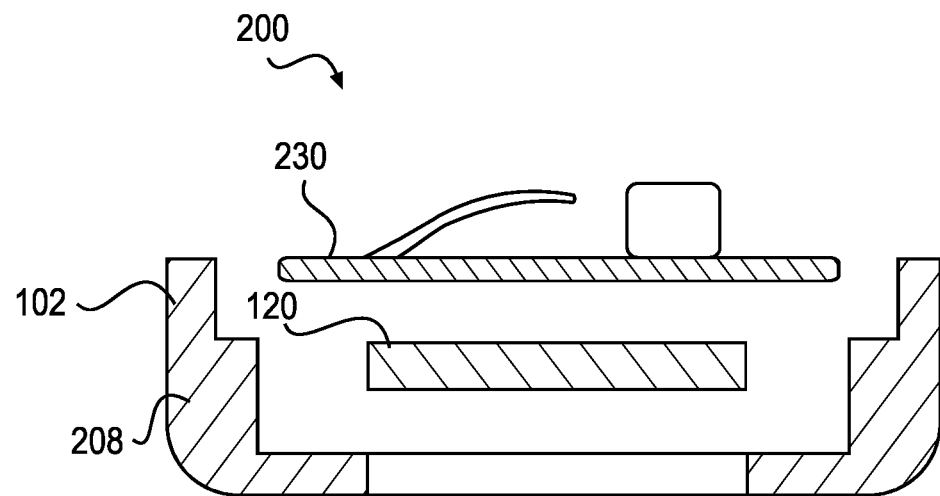
FIG. 11A is a cross-section of a body, a PCB, and a retainer.

FIG. 11A is a cross-section of body 102, PCB 120, and retainer 230 of FIG. 10 aligned while separated from each other in an "exploded" view. In this example, body 102 comprises a retention feature 208, formed as part of body 102, whose function is to be deformed, for example, by thermal forming or ultrasonic staking, so as to cover a portion of retainer 230, in particular a portion of one or more of tabs 234.

Figure 11B:
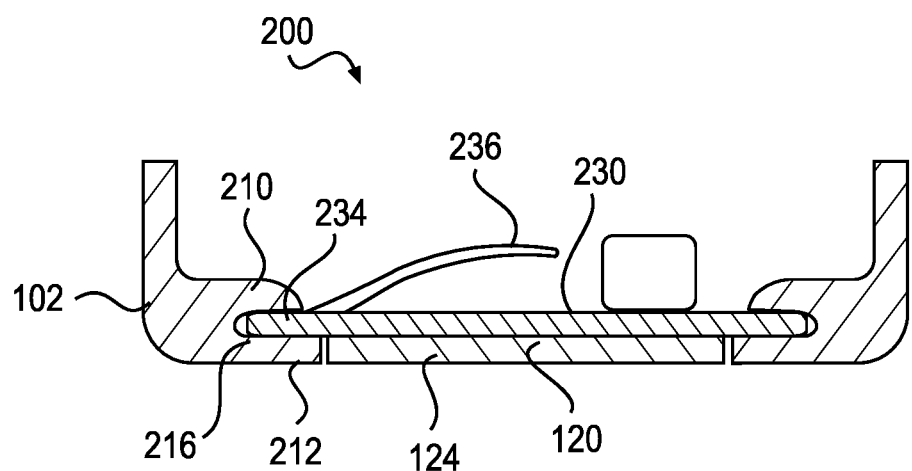
FIG. 11B depicts the items of FIG. 11A after assembly.

FIG. 11B is a cross-section of body 102, the PCB 120, and retainer 230 of FIG. 11A after they have been assembled into assembly 200. In this example, surface 216 is coincident with a second surface of body 102. In this example, retention feature 208 of FIG. 11A has been deformed, for example, by thermal forming or ultrasonic staking, so as to cover a portion of retainer 230, in particular a portion of one or more of tabs 234. In one aspect, other retention mechanisms, for example, the application of an adhesive or sealant over one or more of tabs 234 and a portion of body 102, is used to retain retainer-PCB subassembly in the frame.

Figure 13A:
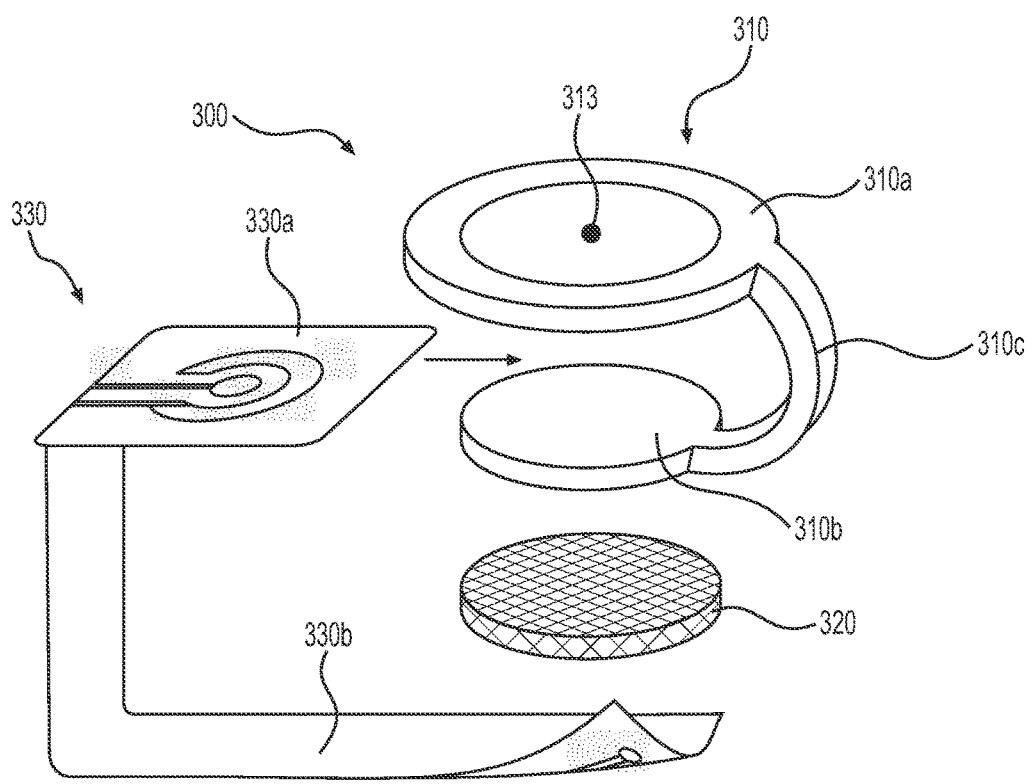
FIG. 13A depicts an exploded view of an assembly comprising a flexible frame with one end of a printed film inserted between upper and lower sections of the frame and the other end of the printed film wrapped around the underside of a compressible spring attached to the bottom of the frame, in accordance with the present disclosure.

FIG. 13A is an exploded view of an assembly 300 comprising a body 310 having an upper section 310a and a lower section 310b joined by a flexible arm 310c. Upper section 310a comprises an opening 313 that, in this example, is a circular through-hole. Lower section 310b is attached on its underside surface to a compressible spring element 320 which allows for movement of both lower section 310b and flexible arm 310c when downward pressure is applied. In an aspect, upper section 310a and lower section 310b may be reversibly secured by way of a tab or other locking mechanism. In an aspect, assembly 300 is formed into a cap as PCB 120 (e.g. shown in FIG. 2) that can be inserted into body 102.

Assembly 300 further comprises a printed film 330 having a tabbed section 330a and a non-tabbed section 330b. A center electrode 350a and an outer electrode 350b (e.g. shown in FIG. 13B) have been printed on the upper face of tabbed section 330a. In this example, tabbed section 330a is inserted between upper section 310a and lower section 310b so that, upon full insertion, electrodes 350a and 350b (e.g. shown in FIG. 13B) are exposed on the upper surface of body 310 through opening 313. The non-tabbed section 330b is folded or bent so that the end of non-tabbed section 330b is wrapped around, and may be attached to, the underside surface of compressible spring element 320. In an aspect, body 310 having electrodes 350a and 350b (e.g. shown in FIG. 13B) exposed through opening 313 is pressed against the skin of a patient to make an SEM measurement.

Figure 13B:
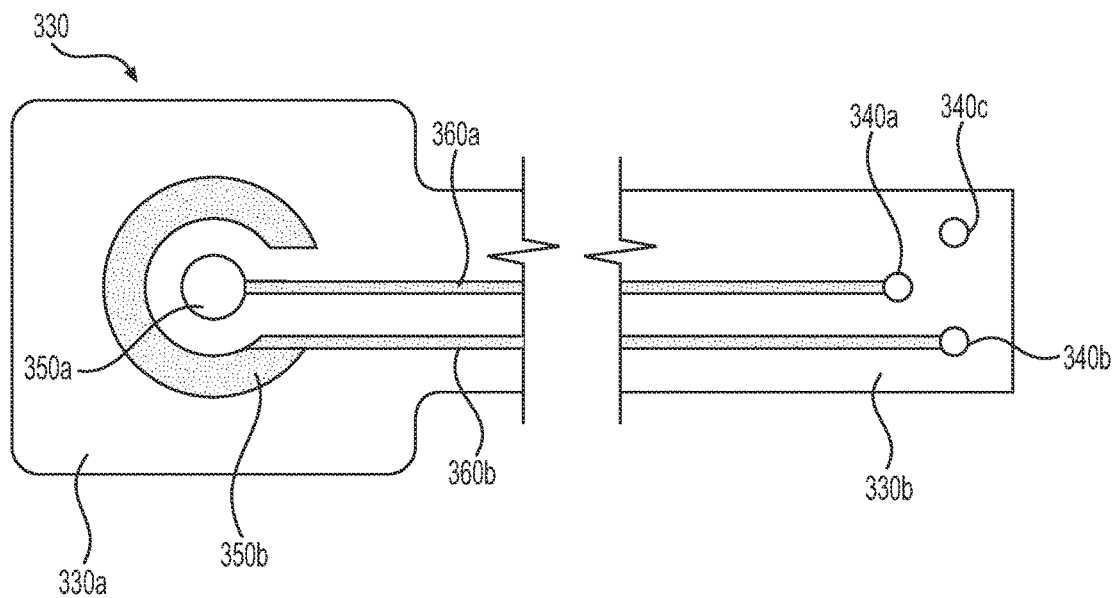
FIG. 13B depicts a top view of one face of an unfolded, printed film, in accordance with the present disclosure.

FIG. 13B is a top view of one side of printed film 330 prior to bending or folding. In this example, non-tabbed section 330b of printed film 330 comprises three contact pads 340a, 340b, and 340c. Center electrode 350a is connected via a conductive trace 360a to contact pad 340a. Similarly, outer electrode 350b is connected via a conductive trace 360b to contact pad 340b. When upper section of 310a (e.g. shown in FIG. 13A) is pressed upon a patient's skin, measurements can be taken by electrodes 350a and 350b.

In an aspect, printed film 330 comprises a flexible plastic material. In a related aspect, the flexible plastic material is selected from the group consisting of polyethylene naphthalene (PEN), polycarbonate (PC), polyethylene terephthalate (PET), polyarylate (PAR), polyethersulfone (PES), fluorene polyester (FPE), polyimide (PI), and combinations thereof. In another aspect, printed film 330 comprises a non-plastic flexible material.

In an aspect, printed film 330 has a thickness of 0.5 mm (0.02 inches). In an aspect, printed film 330 has a thickness of 0.4 mm (0.016 inches). In an aspect, printed film 330 has a thickness of 0.3 mm (0.012 inches). In an aspect, printed film 330 has a thickness of 0.25 mm (0.01 inches). In an aspect, printed film 330 has a thickness of at least 0.2 mm (0.008 inches). In an aspect, printed film 330 has a thickness of at least 0.5 mm (0.02 inches). In an aspect, printed film 330 has a thickness of at least 0.4 mm (0.016 inches). In an aspect, printed film 330 has a thickness of at least 0.3 mm (0.012 inches). In an aspect, printed film 330 has a thickness of at least 0.25 mm (0.01 inches). In an aspect, printed film 330 has a thickness of at least at least 0.2 mm (0.008 inches).

In an aspect, printed film 330 has a thickness that is between 0.4 and 0.5 mm (0.02 and 0.016 inches). In an aspect, printed film 330 has a thickness that is between 0.3 and 0.4 mm (0.012 and 0.016 inches). In an aspect, printed film 330 has a thickness that is between 0.2 and 0.3 mm (0.008 and 0.012 inches). In an aspect, printed film 330 has a thickness that is between 0.25 and 0.35 mm (0.01 and 0.014 inches). In an aspect, printed film 330 has a thickness that is between 0.2 and 0.5 mm (0.008 and 0.02 inches).

In an aspect, printed film 330 is cut from a larger flexible sheet. In an aspect, electrodes 350a and 350b, conductive traces 360a and 360b, and contact pads 340a, 340b, and 340c are printed onto one face of a larger flexible sheet prior to cutting. In an aspect, more than one printed film 330 is cut from the same flexible sheet. In an aspect, conductive ink is used to print electrodes 350a and 350b, conductive traces 360a and 360b, and contact pads 340a, 340b, and 340c onto one face of a flexible sheet prior to cutting. In an aspect, electrodes 350a and 350b, conductive traces 360a and 360b, and contact pads 340a, 340b, and 340c are printed onto one face of a flexible sheet by a 2D or 3D printing process known in the art that is suitable for the manufacture of printed electronics. In an aspect, each printed film 330 is die-cut from a larger flexible sheet. In an aspect, electrodes 350a and 350b, conductive traces 360a and 360b, and contact pads 340a, 340b, and 340c are printed on a pre-cut piece of film.

From the foregoing, it will be appreciated that the present invention can be embodied in various ways, which include but are not limited to the following:

Embodiment 1. A detachable element for use with a reusable component having a retention groove and an alignment guide and a planar contact surface parallel to the retention groove, the detachable element comprising: a body comprising a retention feature configured to engage the retention groove; and an electrical contactor coupled to the body, where the contactor comprises a cantilever element that is configured to touch the planar contact surface when the retention feature is engaged with the retention groove, where the cantilever element is configured to slide along the contact surface as the detachable element is brought together with the reusable component.

Embodiment 2. The detachable element of embodiment 1, where the detachable element is brought together with the reusable component along a path that is perpendicular to the planar contact surface.

Embodiment 3. The detachable element of embodiment 1, where the retention feature extends around a portion of a circumference of the detachable element.

Embodiment 4. The detachable element of embodiment 1, where the body comprises an alignment feature that is configured to mate with the alignment guide of the reusable component, where the retention feature cannot engage the retention groove when the alignment feature is not mated with the alignment guide.

Embodiment 5. The detachable element of embodiment 1, where the body further comprises a sensor comprising two electrodes, where the sensor is in electrical connection with the electrical contactor.

Embodiment 6. The detachable element of embodiment 5, where the body further comprises an insulating cover layer disposed above the sensor.

Embodiment 7. The detachable element of embodiment 1, where the body further comprises a light sensor and a light emitting source, where the light sensor and light emitting source are in electrical connection with the electrical contactor.

Embodiment 8. The detachable element of embodiment 1, where the light emitting source comprises dual emitters configured for emitting 660 nm and 880 nm light.

Embodiment 9. A connector comprising: a reusable component comprising a retention groove and an electrical contact surface that is parallel to the retention groove; and a detachable element comprising a body with a retention feature configured to engage the retention groove and an electrical contactor coupled to the body, where the contactor comprises a compliant element that is configured to touch the contact surface of the reusable element when the retention feature of the detachable element is engaged with the retention groove of the reusable component and to slide along the contact surface as the detachable element is brought together with the reusable component.

Embodiment 10. The connector of embodiment 9, where the body of the reusable component comprises an alignment guide; the detachable element comprises an alignment feature that is configured to mate with alignment guide when the retention feature of the detachable element is engaged with the retention groove of the reusable component; and the retention feature cannot engage the retention groove when the alignment feature is not mated with the alignment guide.

Embodiment 11. The connector of embodiment 9, where the compliant element comprises: a base segment coupled to the body, a first linear segment coupled to the base segment, a second linear segment coupled to the first linear segment, and a contact segment coupled to the second linear segment, where compression of the compliant element in a first direction induces motion of the contact segment in a second direction that is perpendicular to the first direction.

Embodiment 12. A detachable element, comprising: a body comprising a hole and a retention pocket, where the retention pocket comprises a reference surface; and a printed circuit board assembly (PCBA) comprising a printed circuit board (PCB) having an outer edge and a contactor coupled to the PCB, where a portion of the contactor extends beyond the outer edge of the PCB, where the portion of the contactor that extends beyond the outer edge of the PCB is in contact with the reference surface.

Embodiment 13. The detachable element of embodiment 12, where the body comprises a top surface; the PCB comprises a thickness; and the reference surface is parallel to the top surface and offset from the top surface by a distance from the reference surface to the top surface, and the distance is equal to the thickness of the PCB.

Embodiment 14. The detachable element of embodiment 12, where the PCB is a sensor.

Embodiment 15. The detachable element of embodiment 14, where the PCB is selected from the group consisting of a bioimpedance sensor, a photodetector, a temperature sensor, a pH sensor, a perspiration sensor, an ultrasonic sensor, a bone growth stimulator sensor, and a combination thereof.

Embodiment 16. The detachable element of embodiment 12, where the PCB is inserted into the retention pocket and held in place by a retainer comprising a plurality of tabs.

Embodiment 17. The detachable element of embodiment 16, where the retainer is a mechanical positioning element.

Embodiment 18. The detachable element of embodiment 16, where the retainer is a conductive circuit element.

Embodiment 19. The detachable element of embodiment 16, where the retainer comprises one or more conductive elements and one or more non-conductive elements.

Embodiment 20. The detachable element of embodiment 16, where the retainer comprises a deformable retention feature configured to cover a portion of one or more tabs of the retainer.

Embodiment 21. The detachable element of embodiment 5, where the two electrodes consist of one central electrode and one toroidal electrode, wherein the central electrode and toroidal electrode have a concentric orientation.

Embodiment 22. The detachable element of embodiment 21, where the central electrode has a diameter of about 4.318 mm (0.17 inches).

Embodiment 23. The detachable element of embodiment 21, where the toroidal electrode has an inner diameter of about 10.16 mm (0.4 inches) and an outer diameter of about 12.7 mm (0.5 inches).

Embodiment 24. The detachable element of embodiment 21, further comprising a ground plane, where the distance between the two electrodes and the ground plane is about 0.4064 mm (0.016 inches).

Embodiment 25. The detachable element of embodiment 21, where the two electrodes are separated by a gap of about 2.921 mm (0.0115 inches).

Embodiment 26. The detachable element of embodiment 24, wherein the ground plane has a diameter of about 12.7 mm (0.5 inches).

Embodiment 27. A detachable element, comprising: a body comprising an upper section and a lower section joined by a flexible arm, where the upper section comprises an opening and the lower section is attached on its underside to a compressible spring; and a printed film having tabbed and non-tabbed areas and first and second faces, where the tabbed area comprises a sensor comprising two electrodes on its first face, and where the tabbed area is inserted between the upper and lower sections so that the sensor is visually aligned with the opening.

Embodiment 28. The detachable element of embodiment 27, where the non-tabbed area comprises at least two contact pads on its first face.

Embodiment 29. The detachable element of embodiment 28, where each of the at least two contact pads is conductively linked to either of the two electrodes.

Embodiment 30. The detachable element of embodiment 28, where some of the at least two contact pads are conductively linked to either of the two electrodes.

Embodiment 31. The detachable element of embodiment 27, where the second face of the non-tabbed area is wrapped around the compressible spring.

Embodiment 32. The detachable element of embodiment 27, where the second face of the non-tabbed area is attached to the compressible spring.

Embodiment 33. The detachable element of embodiment 27, where the upper and lower sections are releasably secured to the printed film.

While the invention has been described with reference to particular embodiments, it will be understood by those skilled in the art that various changes may be made and equivalents may be substituted for elements thereof without departing from the scope of the invention. In addition, many modifications may be made to a particular situation or material to the teachings of the invention without departing from the scope of the invention. Therefore, it is intended that the invention not be limited to the particular embodiments disclosed but that the invention will include all embodiments falling within the scope and spirit of the appended claims.

We claim:

1. A detachable element for use with a reusable component having a retention groove and an alignment guide and a planar contact surface parallel to the retention groove, the detachable element comprising:
    a body comprising one or more sensors and a retention feature configured to engage the retention groove; and
    an electrical contactor coupled to the body, wherein the contactor comprises a cantilever element that is configured to touch the planar contact surface when the retention feature is engaged with the retention groove, and wherein the cantilever element is configured to slide along the contact surface as the detachable element is brought together with the reusable component,
    wherein each of the one or more sensors comprises two or more electrodes, wherein each of the one or more sensors is in electrical connection with the electrical contactor, and wherein the two or more electrodes comprise one central electrode and one toroidal electrode, wherein the central electrode and toroidal electrode have a concentric orientation.

2. The detachable element of claim 1, wherein the detachable element is brought together with the reusable component along a path that is perpendicular to the planar contact surface.

3. The detachable element of claim 1, wherein the retention feature extends around a portion of a circumference of the detachable element.

4. The detachable element of claim 1, wherein the body comprises an alignment feature that is configured to mate with the alignment guide of the reusable component, wherein the retention feature cannot engage the retention groove when the alignment feature is not mated with the alignment guide.

5. The detachable element of claim 1, wherein the body further comprises an insulating cover layer disposed above the one or more sensors.

6. The detachable element of claim 1, wherein the central electrode has a diameter of about 4.318 mm (0.17 inches).

7. The detachable element of claim 1, wherein the toroidal electrode has an inner diameter of about 10.16 mm (0.4 inches) and an outer diameter of about 12.7 mm (0.5 inches).

8. The detachable element of claim 1, where the central electrode and the toroidal electrode is separated by a gap of about 2.921 mm (0.0115 inches).

9. The detachable element of claim 1, wherein the body further comprises a light sensor and a light emitting source, wherein the light sensor and light emitting source are in electrical connection with the electrical contactor.

10. The detachable element of claim 9, wherein the light emitting source comprises dual emitters configured for emitting 660 nm and 880 nm light.

11. The detachable element of claim 1, further comprising a ground plane, wherein the distance between the two or more electrodes and the ground plane is about 0.4064 mm (0.016 inches).

12. The detachable element of claim 11, wherein the ground plane has a diameter of about 12.7 mm (0.5 inches).

13. A connector comprising:
a reusable component comprising a retention groove and an electrical contact surface that is parallel to the retention groove; and
a detachable element comprising:
   a body with a retention feature configured to engage the retention groove and an electrical contactor coupled to the body, wherein the contactor comprises a compliant element that is configured to touch the contact surface of the reusable element when the retention feature of the detachable element is engaged with the retention groove of the reusable component and to slide along the contact surface as the detachable element is brought together with the reusable component, and
   one or more sensors, wherein each of the one or more sensors comprises two or more electrodes, and wherein the two or more electrodes comprise one central electrode and one toroidal electrode, wherein the central electrode and toroidal electrode have a concentric orientation.

14. The connector of claim 13, wherein:
the body of the reusable component comprises an alignment guide;
the detachable element comprises an alignment feature that is configured to mate with the alignment guide when the retention feature of the detachable element is engaged with the retention groove of the reusable component; and
the retention feature cannot engage the retention groove when the alignment feature is not mated with the alignment guide.

15. The connector of claim 13, wherein:
the compliant element comprises:
   a base segment coupled to the body,
   a first linear segment coupled to the base segment,
   a second linear segment coupled to the first linear segment, and
   a contact segment coupled to the second linear segment,
wherein compression of the compliant element in a first direction induces motion of the contact segment in a second direction that is perpendicular to the first direction.

16. The connector of claim 13, wherein the one or more sensors is selected from a group consisting of a bioimpedance sensor, a photodetector, a temperature sensor, a pH sensor, a perspiration sensor, an ultrasonic sensor, a bone growth stimulator sensor, and combinations thereof.

17. The connector of claim 13, further comprising a printed circuit board assembly (PCBA) coupled to the body, comprising a printed circuit board (PCB) having a top surface, wherein the top surface comprises a plurality of conductive planar contact surfaces.

18. A detachable element comprising:
a body comprising an upper section and a lower section joined by a flexible arm, wherein the upper section comprises an opening and the lower section is attached on its underside to a compressible spring; and
a printed film comprising tabbed and non-tabbed areas and first and second faces, wherein
the tabbed area comprises a sensor comprising two electrodes on its first face,
the tabbed area is inserted between the upper and lower sections so that the sensor is visually aligned with the opening,
the non-tabbed area comprises at least two contact pads on its first face, and
some of the at least two contact pads are conductively linked to either of the two electrodes.

* * * * *